(12) United States Patent
Nishie et al.

(10) Patent No.: US 12,421,526 B2
(45) Date of Patent: Sep. 23, 2025

(54) AAV MUTANT HAVING BRAIN-TARGETING PROPERTY

(71) Applicant: TAKARA BIO INC., Shiga (JP)

(72) Inventors: Toshikazu Nishie, Kusatsu (JP); Fuyuko Takashima, Kusatsu (JP); Tatsuji Enoki, Kusatsu (JP); Junichi Mineno, Kusatsu (JP); Yoshinori Tanaka, Kusatsu (JP)

(73) Assignee: TAKARA BIO INC., Shiga (JP)

( * ) Notice: Subject to any disclaimer, the term of this patent is extended or adjusted under 35 U.S.C. 154(b) by 990 days.

(21) Appl. No.: 17/442,386

(22) PCT Filed: Apr. 23, 2020

(86) PCT No.: PCT/JP2020/017495
§ 371 (c)(1),
(2) Date: Sep. 23, 2021

(87) PCT Pub. No.: WO2020/218419
PCT Pub. Date: Oct. 29, 2020

(65) Prior Publication Data
US 2022/0162637 A1   May 26, 2022

(30) Foreign Application Priority Data
Apr. 24, 2019   (JP) .................. 2019-082417

(51) Int. Cl.
*C12N 15/86*   (2006.01)
*C07K 14/015*  (2006.01)
*C12N 7/00*    (2006.01)

(52) U.S. Cl.
CPC ............ *C12N 15/86* (2013.01); *C07K 14/015* (2013.01); *C12N 7/00* (2013.01); *C12N 2710/10041* (2013.01)

(58) Field of Classification Search
CPC ................. C12N 15/86; C12N 7/00; C12N 2710/10041; C07K 14/015
See application file for complete search history.

(56) References Cited

U.S. PATENT DOCUMENTS

| | | | |
|---|---|---|---|
| 9,938,541 B2 * | 4/2018 | Nishie | C12N 15/86 |
| 2007/0238684 A1 | 10/2007 | Hallek et al. | |
| 2013/0142764 A1 | 6/2013 | Davidson et al. | |
| 2014/0294771 A1 | 10/2014 | Schaffer et al. | |
| 2015/0315610 A1 | 11/2015 | Nishie et al. | |
| 2016/0123990 A1 | 5/2016 | High et al. | |
| 2017/0029464 A1 | 2/2017 | Körbelin et al. | |
| 2018/0135076 A1 | 5/2018 | Linden | |
| 2022/0038609 A1 | 2/2022 | Zhao et al. | |

FOREIGN PATENT DOCUMENTS

| | | | | |
|---|---|---|---|---|
| CN | 109476707 | | 3/2019 | |
| EP | 2940131 A1 | * | 11/2015 | .......... C07K 14/005 |
| JP | 2017-513486 | | 6/2017 | |
| RU | 2 611 202 | | 2/2017 | |
| RU | 2016 104 614 | | 8/2017 | |
| RU | 2016 133 623 | | 3/2018 | |
| WO | 2010/114143 | | 10/2010 | |
| WO | 2012/145601 | | 10/2012 | |
| WO | 2013/014764 | | 1/2013 | |
| WO | 2014/103957 | | 7/2014 | |
| WO | 2015/006743 | | 1/2015 | |
| WO | 2015/121501 | | 8/2015 | |
| WO | 2017/197355 | | 11/2017 | |
| WO | WO-2017197355 A2 | * | 11/2017 | .......... A61K 39/235 |
| WO | 2020/114143 | | 6/2020 | |

OTHER PUBLICATIONS

Office Action and Search Report issued Jun. 13, 2023 in corresponding Russian Patent Application No. 2021133906, with English translation of Office Action and Search Report.
Gao, G. et al., "Clades of Adeno-Associated Viruses Are Widely Disseminated in Human Tissues", Journal of Virology, vol. 78, No. 12, pp. 6381-6388, 2004.
Adachi, K. et al., "A New Recombinant Adeno-Associated Virus (Aav)-Based Random Peptide Display Library System: Infection-Defective AAV1.9-3 as a Novel Detargeted Platform for Vector Evolution", Gene Ther Regul., vol. 5, pp. 31-55, 2010.
English translation of International Preliminary Report on Patentability issued Sep. 28, 2021 in corresponding International (PCT) Patent Application No. PCT/JP2020/017495.
(Continued)

*Primary Examiner* — Anoop K Singh
*Assistant Examiner* — Zanna Maria Beharry
(74) *Attorney, Agent, or Firm* — Wenderoth, Lind & Ponack, L.L.P.

(57) ABSTRACT

The present invention provides a nucleic acid which encodes an adeno-associated virus (AAV) capsid protein mutant that contains a peptide comprising an amino acid sequence selected from the group consisting of SEQ ID Nos. 15 to 62 or a peptide comprising an amino acid sequence produced by substituting, deleting, inserting and/or adding one or several amino acid residues in an amino acid sequence selected from the group consisting of SEQ ID Nos. 15 to 62; DNA comprising the nucleic acid; a cell harboring the DNA; and a method for producing the cell.

5 Claims, 2 Drawing Sheets

Specification includes a Sequence Listing.

(56) References Cited

OTHER PUBLICATIONS

International Search Report issued Jul. 28, 2020 in corresponding International (PCT) Patent Application No. PCT/JP2020/017495.
Office Action issued Dec. 1, 2023 in corresponding Chinese Patent Application No. 202080030827.0, with English translation, 17 pages.
Office Action issued Oct. 10, 2023 in corresponding Japanese Patent Application No. 2021-516202, with English translation.
Extended European Search Report issued Oct. 23, 2023 in corresponding European Patent Application No. 20795029.6.
Castle et al., "Controlling AAV Tropism in the Nervous System with Natural and Engineered Capsids", Methods Mol Biol., 2016, vol. 1382, pp. 133-149.
Office Action issued Apr. 23, 2025 in the corresponding Australian Patent Application No. 2020263757.
Office Action issued Jul. 15, 2025 in corresponding Canadian Patent Application No. 3132447.

* cited by examiner

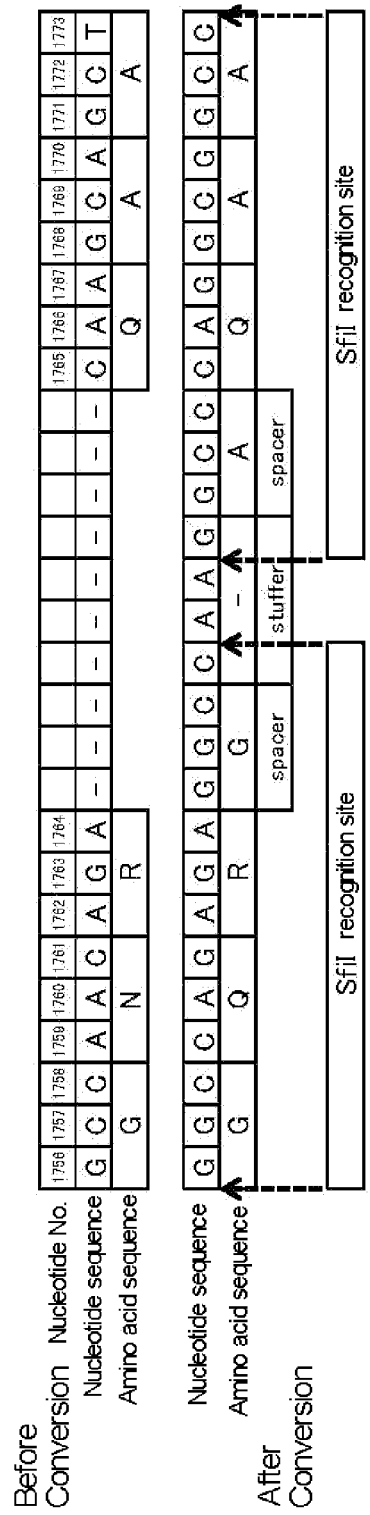
[FIG. 1]

[FIG. 2]
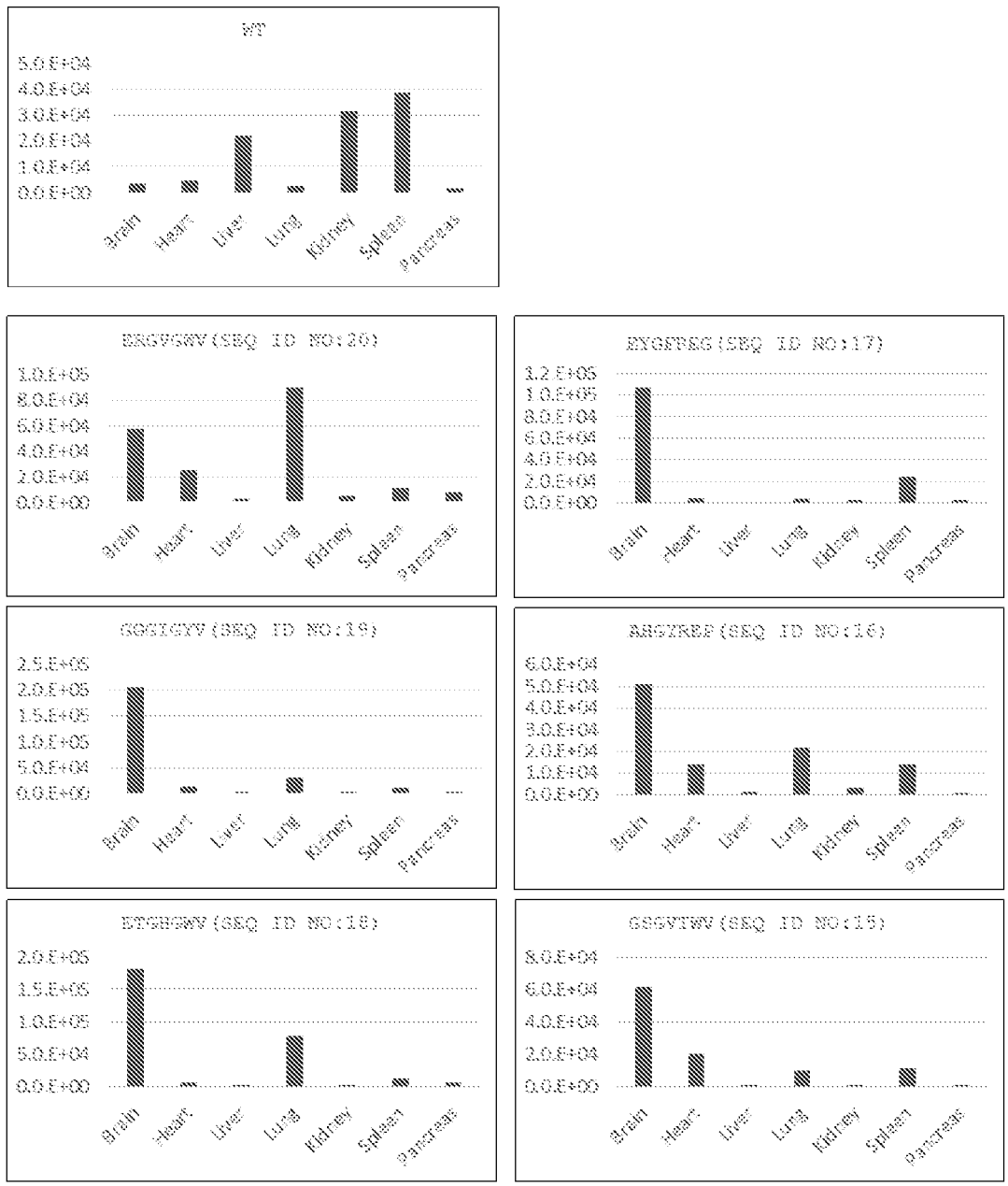

AAV MUTANT HAVING BRAIN-TARGETING PROPERTY

TECHNICAL FIELD

The present invention relates to a nucleic acid encoding a mutant of an adeno-associated virus (AAV) capsid protein which has tropism for brain, an AAV particle comprising the capsid protein variant, and a method of producing a gene-transduced cell by use of the particle.

BACKGROUND ART

AAV is a virus having a linear single-stranded DNA genome of 4.7 kb, comprising open reading frames of two genes rep and cap. The rep gene encodes four proteins necessary for genome replication (Rep78, Rep68, Rep52, and Rep40). The cap gene expresses three capsid proteins that assemble for formation of a viral capsid (VP1, VP2, VP3), and assembly-activating protein (AAP). Replication of AAV in nature relies on the presence of a helper virus such as an adenovirus or a herpes virus. In the absence of a helper virus, the genome of AAV is maintained in an episome or integrated into a chromosome of a host, so that the AAV is present in a latent state. Over one hundred serotypes and clades (non-patent literature 1) of AAV are currently identified. Particularly, development of vectors for gene delivery based on AAV2 is advanced.

In 1989, a gene delivery vector system based on AAV2 was developed for the first time. Vectors based on AAV have been found to have many advantages. Since wild-type AAV is nonpathogenic and has no etiological relation to any known diseases, vectors based on AAV are believed to be extremely safe. In addition, AAV has high gene transduction efficiency.

Administration of AAV particles enables long-period and stable gene transduction into various target organs and target cells. Until now, gene transduction with high efficiency into skeletal muscles, liver (hepatic cells), heart (cardiac muscle cells), nerve cells, pancreatic gland cells, and pancreatic islet cells has been reported. In addition, AAV has been used in human clinical trials. On the other hand, an attempt to change the cell tropism of AAV by alteration of capsid proteins of the AAV and an attempt to avoid removal of AAV particles by neutralizing antibodies have been made. For example, AAV capsids with tropism for specific organs and cells such as neuroglia cells, airway epithelial cells, coronary artery vascular endothelial cells, and lung, and AAV capsids with tropism for tumor cells such as glioblastoma cells, melanoma cells, lung cancer cells, and breast cancer cells have been created (non-patent literature 2).

CITATION LIST

Non-Patent Literatures

Non-patent literature 1: Gao et al., J. Virology, Vol. 78, pp. 6381-6388, 2004

Non-patent literature 2: Adachi K. et al., Genen Ther. Regul., Vol. 5, pp. 31-55, 2010

SUMMARY OF INVENTION

Problem to be Solved by the Invention

Objections of the present invention includes provision of an AAV capsid protein mutant with tropism for a brain, and provision of a method of efficiently introducing a gene into a brain.

Solutions to the Problems

The present inventors intensively made efforts to solve the above-described problems, and as a result, created a desired AAV particle, wherein the AAV particle comprises an AAV capsid protein comprising an amino acid sequence selected from the group consisting of SEQ ID NOS: 15-62. Thus the present invention was completed.

The present invention generally relates to:

[1] A nucleic acid encoding a mutant of an adeno-associated virus (AAV) capsid protein which comprises a peptide comprising an amino acid sequence selected from the group consisting of SEQ ID NOs: 15-62 or a peptide comprising an amino acid sequence that differs from an amino acid sequence selected from the group consisting of SEQ ID NOs: 15-62 by substitution, deletion, insertion and/or addition of one or several amino acids;

[2] The nucleic acid according to [1], wherein the AAV capsid protein is derived from AAV2;

[3] The nucleic acid according to [2], wherein the peptide is placed at a position between amino acid number 588 and amino acid number 589 in VP1 of AAV2;

[4] A recombinant DNA comprising the nucleic acid according to any one of [1] to [3];

[5] A cell comprising the nucleic acid according to any one of [1] to [3] or the recombinant DNA according to [4];

[6] An AAV particle comprising a mutant of an AAV capsid protein which comprises a peptide comprising an amino acid sequence selected from the group consisting of SEQ ID NOS: 15-62 or a peptide comprising an amino acid sequence that differs from an amino acid sequence selected from the group consisting of SEQ ID NOS: 15-62 by substitution, deletion, insertion and/or addition of one or several amino acids;

[7] The AAV particle according to [6], wherein the AAV capsid protein is derived from AAV2;

[8] The AAV particle according to [7], wherein the peptide is placed at a position between amino acid number 588 and amino acid number 589 in VP1 of AAV2;

[9] A method of producing a gene-transduced cell, the method comprising a step of bringing an AAV particle comprising a mutant of an AAV capsid protein which comprises a peptide comprising an amino acid sequence selected from the group consisting of SEQ ID NOs: 15-62 or a peptide comprising an amino acid sequence that differs from an amino acid sequence 15 selected from the group consisting of SEQ ID NOS: 15-62 by substitution, deletion, insertion and/or addition of one or several amino acids, into contact with a cell;

[10] The method according to [9], wherein the AAV capsid protein is derived from AAV2; and

[11] The method according to [10], wherein the peptide is placed at a position between amino acid number 588 and amino acid number 589 in VP1 of AAV2.

Effects of the Invention

According to the present invention, a gene transduction system useful for gene transduction into brain is provided. The AAV particle of the present invention has high cell tropism for brain, and a gene transduced by the AAV particle can be strongly expressed.

BRIEF DESCRIPTION OF DRAWINGS

FIG. 1 shows a method of producing a nucleic acid construct for enabling a capsid protein to comprise a random peptide.

FIG. 2 shows evaluation results of the tropism of AAV capsid protein mutants of the present invention.

MODE FOR CARRYING OUT THE INVENTION

As used herein, the "adeno-associated virus" refers to a small virus belonging to the genus Dependovirus which lies within the family Parvoviridae and capable of infecting primates including human and other mammals. Hereinafter, the adeno-associated virus is abbreviated as AAV. AAV has a non-enveloped shell (capsid) of a regular icosahedron and a linear single-stranded DNA inside the shell. As used herein, AAV includes the wild-type virus and derivatives thereof, and includes all serotypes and clades of AAV unless specified otherwise.

The "vector" as used herein means a molecule or an associated molecule that is used for mediating delivery of a polynucleotide to a cell and which comprises the polynucleotide or associates with the polynucleotide. Examples of the vector include vector DNAs such as plasmid vectors and phage vectors, viral vector particles, liposomes, and other vehicles for gene delivery, unless specified otherwise.

The "capsid protein" as used herein means a protein that is encoded by the cap gene present in the genome of AAV and constitutes the capsid of AAV. The wild-type AAV genome encodes three capsid proteins, and there are VP1, VP2 and VP3. As used herein, the capsid protein includes VP1, VP2 and VP3.

As used herein, the term "several" in the context of substitution, deletion, insertion and/or addition of amino acids means, for example, 2, 3, 4, 5, 6, 7, 8 or 9 amino acids depending on the length of a reference amino acid sequence.

(1) Nucleic Acid Encoding an AAV Capsid Protein Mutant

The nucleic acid of the present invention encodes a mutant of an AAV capsid protein which comprises a peptide comprising an amino acid sequence selected from the group consisting of SEQ ID NOS: 15-62 or a peptide comprising an amino acid sequence that differs from an amino acid sequence selected from the group consisting of SEQ ID NOS: 15-62 by substitution, deletion, insertion and/or addition of one or several amino acids. Preferably, the nucleic acid of the present invention encodes an AAV capsid protein mutant that comprises a peptide comprising an amino acid sequence selected from the group consisting of SEQ ID NO: 15 to SEQ ID NO: 62. More preferably, the nucleic acid of the present invention encodes an AAV capsid protein mutant that comprises a peptide comprising an amino acid sequence selected from the group consisting of SEQ ID NO: 15, SEQ ID NO: 16, SEQ ID NO: 17, SEQ ID NO: 18, SEQ ID NO: 19 and SEQ ID NO: 20, or a peptide comprising an amino acid sequence that differs from an amino acid sequence selected from the group consisting of SEQ ID NO: 15, SEQ ID NO: 16, SEQ ID NO: 17, SEQ ID NO: 18, SEQ ID NO: 19 and SEQ ID NO: 20 by substitution, deletion, insertion and/or addition of one or several amino acids. The peptide comprising an amino acid sequence that differs from an amino acid sequence shown by the above-mentioned SEQ ID NOs by substitution, deletion, insertion and/or addition of one or several amino acids, when comprised in an AAV capsid protein, retains the cell tropism of an AAV capsid protein mutant that comprises a peptide comprising an amino acid sequence shown by the above-mentioned SEQ ID NOS. In other words, the number of amino acids to be substituted, deleted, inserted and/or added in an amino acid sequence shown by the above-mentioned SEQ ID NOs is not limited as long as the cell tropism that a peptide comprising an amino acid sequence shown by the above-mentioned SEQ ID NOs confers to the AAV capsid protein mutant comprising the peptide is retained. For example 1 to 5, preferably 1 to 4, more preferably 1, 2 or 3 amino acids may be substituted, deleted and/or inserted. For example 1 to 9, preferably 1 to 8, more preferably 1 to 7, still more preferably 1 to 6, still more preferably 1 to 5, still more preferably 1, 2, 3 or 4 amino acids may be added.

For example, the peptide to be comprised in the AAV capsid protein mutant may be a peptide comprising an amino acid sequence having at least 70%, at least 75%, at least 80%, at least 85%, or at least 90% identity with an amino acid sequence selected from the group consisting of SEQ ID NO: 15 to SEQ ID NO: 62. The peptide comprising an amino acid sequence having at least 70%, at least 75%, at least 80%, at least 85%, or at least 90% identity with an amino acid sequence shown by the above-mentioned SEQ ID NOS, when comprised in an AAV capsid protein, retains the cell tropism of an AAV capsid protein mutant comprising a peptide comprising an amino acid sequence shown by the above-mentioned SEQ ID NOS.

For example, the peptide to be comprised in the AAV capsid protein mutant may be a peptide comprising an amino acid sequence shown by:

formula I:
$X^1X^2GX^3GWV$;

formula II:
$X^4X^5X^6x^7GWV$;

formula III:
$X^8X^9GX^{10}X^{11}WV$;

formula IV:
$X^{12}X^{13}GX^{14}GX^{15}V$;

formula V:
$X^{16}X^{17}GX^{18}GWX^{19}$;
or formula VI:
$X^{20}X^{21}GX^{22}REX^{23}$, wherein each of $X^1$ to $X^{23}$ is any amino acid residue, G represents glycine, W represents tryptophan, V represents valine, R represents arginine, and E represents glutamic acid. Preferably, in formula I ($X^1X^2GX^3GWV$), $X^1$ is E (glutamic acid), G (glycine) or T (threonine), and $X^2$ is R (arginine), T (threonine), S (serine), N (asparagine), E (glutamic acid) or D (aspartic acid), and $X^3$ is V (valine), H (histidine), R, M (methionine) or L (leucine). Preferably, in formula II ($X^4X^5X^6x^7GWV$), $X^4$ is A (alanine) or E, $X^5$ is D, G or A, $X^6$ is K (lysine), Q (glutamine) or N, and $X^7$ is V or L. Preferably, in formula III ($X^8X^9GX^{10}X^{11}WV$), $X^8$ is A, E or G, $X^9$ is S, D, G or R, $X^{10}$ is T, M, D or V, and $X^{11}$ is R, V, S or T. Preferably, in formula IV ($X^{12}X^{13}GX^{14}GX^{15}V$), $X^{12}$ is D, E, G or R, $X^{13}$ is A, G, D or V, $X^{14}$ is I, H, D, F (phenylalanine), G or L, and $X^{15}$ is Y (tyrosine), F, R, G or V. Preferably, in formula V $(X^{16}X^{17}GX^{18}GWX^{19})$, $X^{16}$ is A, E or G, $X^{17}$ is G, R or S, $X^{18}$ is V, H or D, and $X^{19}$ is T, G, K, I (isoleucine) or A. Preferably, in formula VI $(X^{20}X^{21}GX^{22}REX^{23})$, $X^{20}$ is E or A, $X^{21}$ is Y or H, $X^{22}$ is F or Y, and $X^{23}$ is G or P (proline).

Examples of the peptide comprising an amino acid sequence shown by formula I include, but not limited to, a peptide comprising an amino acid sequence selected from the group consisting of SEQ ID NOS: 18, 20, 21, 22, 46, 55, 59 and 60, and a peptide comprising an amino acid sequence that differs from the amino acid sequence selected from the group consisting of SEQ ID NOs: 18, 20, 21, 22, 46, 55, 59 and 60 by substitution, deletion, insertion and/or addition of 1 to 3 amino acids. Examples of the peptide comprising an amino acid sequence shown by formula II include, but not limited to, a peptide comprising an amino acid sequence selected from the group consisting of SEQ ID NOS: 25, 29 and 32, and a peptide comprising an amino acid sequence that differs from the amino acid sequence selected from the group consisting of SEQ ID NOs: 25, 29 and 32 by substitution, deletion, insertion and/or addition of 1 to 4 amino acids. Examples of the peptide comprising an amino acid sequence shown by formula III include, but not limited to, a peptide comprising an amino acid sequence selected from the group consisting of SEQ ID NOs: 15, 24, 38, 48 and 54, and a peptide comprising an amino acid sequence that differs from the amino acid sequence selected from the group consisting of SEQ ID NOS: 15, 24, 38, 48 and 54 by substitution, deletion, insertion and/or addition of 1 to 4 amino acids. Examples of the peptide comprising an amino acid sequence shown by formula IV include, but not limited to, a peptide comprising an amino acid sequence selected from the group consisting of SEQ ID NOs: 19, 31, 35, 44, 56 and 58, and a peptide comprising an amino acid sequence that differs from the amino acid sequence selected from the group consisting of SEQ ID NOs: 19, 31, 35, 44, 56 and 58 by substitution, deletion, insertion and/or addition of 1 to 4 amino acids. Examples of the peptide comprising an amino acid sequence shown by formula V include, but not limited to, a peptide comprising an amino acid sequence selected from the group consisting of SEQ ID NOS: 26, 39, 42, 43, 47 and 50, and a peptide comprising an amino acid sequence that differs from the amino acid sequence selected from the group consisting of SEQ ID NOs: 26, 39, 42, 43, 47 and 50 by substitution, deletion, insertion and/or addition of 1 to 4 amino acids. Examples of the peptide comprising an amino acid sequence shown by formula VI include, but not limited to, a peptide comprising an amino acid sequence shown by SEQ ID NO: 16 or 17, and a peptide comprising an amino acid sequence that differs from the amino acid sequence shown by SEQ ID NO: 16 or 17 by substitution, deletion, insertion and/or addition of 1 to 4 amino acids.

The AAV capsid protein mutant encoded by the nucleic acid of the present invention can be prepared by inserting the peptide into an AAV capsid protein of any wild-type AAV, such as AAV type 1 (AAV1), AAV type 2 (AAV2), AAV type 3 (AAV3A, AAV3B etc.), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV11), avian AAV, bovine AAV, canine AAV, equine AAV, or ovine AAV, or replacing a part of the amino acid sequence of the AAV capsid protein with the peptide (in other words, by making the AAV capsid protein comprise the peptide). In the present invention, a capsid protein of AAV2 is preferably used.

The AAV capsid protein mutant encoded by the nucleic acid of the present invention may be a protein comprising substitution, deletion, insertion and/or addition of one or more or several amino acids as well as the above-mentioned peptide in the wild-type AAV capsid protein. The "protein comprising substitution, deletion, insertion and/or addition of one or more or several amino acids as well as the above-mentioned peptide" retains the properties of the original protein, for example the cell tropism of the AAV capsid protein mutant conferred by the above-mentioned peptide, the capsid-forming ability, the function of capsid protein (for example, protection of viral genome, uncoating after entry into host cells) and the like.

Further, a spacer sequence may be added to the N terminal and/or C terminal of the peptide to be comprised in the AAV capsid protein. The spacer sequence preferably consists of 1 to 5 amino acid residues. The amino acid residues constituting the spacer sequence are particularly limited. For example, the spacer sequence may comprise an amino acid selected from the group consisting of glycine, alanine and serine.

As the AAV capsid protein for comprising the peptide, AAV VP1, VP2 or VP3 may be used. Only any one of VP1, VP2 and VP3 may be made to comprise the peptide, or all of VP1, VP2 and VP3 may be made to comprise the peptide. Furthermore, two capsid proteins such as VP1 and VP2, VP2 and VP3, or VP1 and VP3 may be made to comprise the peptide. VP1 to VP3 are encoded by the cap gene region in the AAV genome. In one embodiment of the present invention, a region shared by VP1 to VP3 is made to comprise the peptide so that a mutation can be introduced into all of VP1 to VP3. In another embodiment of the present invention, a gene encoding VP1, VP2 or VP3 is prepared separately from the cap gene region of AAV, and a mutation is introduced into the gene. In this case, a treatment that inhibits a wild-type capsid protein corresponding to a capsid protein encoded by the gene into which a mutation has been introduced from being expressed from the cap gene region of AAV may be performed.

In the case where AAV2 VP1 is used, the AAV capsid protein mutant encoded by the nucleic acid of the present invention preferably comprises the peptide at a position between amino acid number 588 and amino acid number 589. The amino acid number 588 of AAV2 VP1 is arginine. The amino acid number 589 of AAV2 VP1 is glutamine. The amino acid number 588 of AAV2 VP1 corresponds to the amino acid number 451 of AAV2 VP2 and the amino acid number 386 of AAV2 VP3. In the case where a capsid protein of AAV serotypes and clades other than AAV2 is used as the AAV capsid protein, the AAV capsid protein is made to comprise the peptide between amino acids corresponding to amino acid numbers 588 and 589 of AAV2 VP1. A person skilled in the art can easily identify an amino acid of a capsid protein of AAV serotypes and clades other than AAV2 which corresponds to the amino acid at amino acid number 588 of AAV2 VP1. For example, see an alignment of amino acid sequences of VP1 shown in Gao et al., Proc. Natl. Acad. Sci. USA, Vol. 99, No. 18, pp. 11854-11859, 2002. For example, the amino acid number 588 of AAV2 VP1 corresponds to the amino acid number 589 of AAV1, the amino acid number 590 of AAV7, and the amino acid number 591 of AAV8.

The nucleic acid of the present invention may be operably linked to a suitable control sequence. Examples of the control sequence include a promoter sequence, a polyadenylation signal, a transcription termination sequence, an upstream regulatory domain, a replication origin, an internal ribosomal entry site (IRES), and an enhancer. Examples of the promoter sequence include an inducible promoter sequence, and a constitutive promoter sequence. The control sequence may be an endogenous or exogenous sequence of AAV from which the capsid protein originates, a native sequence, or a synthesized sequence. The present invention also includes such a recombinant DNA capable of expressing the AAV capsid protein mutant.

The recombinant DNA of the present invention is useful for delivering the nucleic acid of the present invention to cells in vitro, ex vivo or in vivo and imparting the ability to express the AAV capsid protein mutant to the cells. Then, the cell to which the nucleic acid of the present invention is delivered is useful for producing AAV particles. The recombinant DNA can be particularly used for delivery or introduction of the nucleic acid of the present invention into animal cells, preferably mammal cells.

In the present invention, the recombinant DNA of the present invention can be prepared by making a DNA used as a vector retain the nucleic acid of the present invention. For example, a plasmid DNA, a phage DNA, a transposon, a cosmid DNA, an episomal DNA, or a viral genome can be used.

(2) Cell Containing the Nucleic Acid of the Present Invention

The present invention also provides a host cell, for example an isolated host cell, containing the nucleic acid of the present invention, specifically the recombinant DNA as described in above (1). An isolated cell is, for example, a cell line maintained in vitro. The host cell of the present invention is useful for production of the AAV particle of the present invention, as explained below. When the host cell of the present invention is used for producing AAV particles, the host cell may be referred to as a "packaging cell" or "producer cell". The host cell of the present invention may comprise the recombinant DNA of the present invention as described in above (1) integrated into the genome, or retain the recombinant DNA in the cell so as to transiently express the AAV capsid protein mutant.

Introduction of the recombinant DNA of the present invention into a host cell can be performed by a known method. For example, electroporation, calcium phosphate precipitation, direct microinjection into cells, liposome-mediated gene transfection, or nucleic acid delivery using a high-speed particle gun can be used. When a viral vector is used, an infection method suitable for the vector may be selected. By use of such an established technique, the recombinant DNA of the present invention is introduced stably into a chromosome of a host cell or transiently into a cytoplasm of a host cell. For stable transformation, a selectable marker, for example a well-known selectable marker such as a neomycin resistance gene (encoding neomycin phosphotransferase), or a hygromycin B resistance gene (encoding aminoglycoside phosphotransferase (APH)) may be linked to the recombinant DNA of the present invention.

As the host cell, various cells, for example, mammal cells including mouse cells and primate cells (for example, human cells) or insect cells can be used. Suitable examples of mammal cells include, but not limited to, primary cells and cell lines. Examples of suitable cell lines include 293 cells, COS cells, Hela cells, Vero cells, 3T3 mouse fibroblasts, C3H10T1/2 fibroblasts, CHO cells, and cells derived from them.

(3) AAV Particle Comprising an AAV Capsid Protein Comprising an Amino Acid Sequence Encoded by the Nucleic Acid of the Present Invention The AAV particle of the present invention is an AAV particle comprising an AAV capsid protein mutant comprising the peptide as described in above (1). The AAV particle of the present invention can be produced from the host cell described in above (2). The AAV particle of the present invention has tropism for a brain, and is useful for gene introduction into a brain. The brain includes brain cells such as neuronal cells and glial cells (microglia, oligodendrocytes, astrocytes). The gene introduced by the AAV particle of the present invention is strongly expressed in the above-mentioned tissues, organs and cells.

For production of the AAV particle, a cell comprising some elements necessary for production of AAV particles can be used as a packaging cell. The first element is a vector genome (also referred to as an expression vector) for a recombinant AAV which may be replicated in a host cell and packaged in an AAV particle. The recombinant AAV vector genome comprises a heterologous polynucleotide of interest, and AAV inverted terminal repeat (ITR) sequences located on each side, i.e. 5'- and 3'-sides of the heterologous polynucleotide of interest. The heterologous polynucleotide of interest may have a control sequence for the expression. The nucleotide sequences of ITR sequences are known. For AAV2-ITR sequences, for example, see Human Gene Therapy, Vol. 5, pp. 793-801, 1994. As the AAV ITR sequences, ITR sequences derived from any of various AAV serotypes including AAV1, AAV2, AAV3, AAV4, AAV5, AAV7 and the like can be used. The ITR sequences used in the present invention may be derived from a wild-type AAV or may be altered by insertion, deletion or substitution of a nucleotide(s). The ITR sequences enable replication of the recombinant AAV vector genome in the presence of Rep protein, and enable incorporation of the recombinant AAV vector genome into a capsid particle in the formation of an AAV particle.

The size of the heterologous polynucleotide of interest which can be harbored inside the AAV particle of the present invention is generally less than about 5 kilo bases (kb). The heterologous polynucleotide of interest may be, for example, a gene encoding a protein of interest which a recipient lacks or loses, a gene encoding a protein having a desired biological or therapeutic activity (for example, antimicrobial, antiviral, or antitumor activity), a desired nucleotide sequence encoding RNA that inhibits or decreases production of a harmful or undesired protein, or a nucleotide sequence encoding an antigenic protein. The heterologous polynucleotide of interest can be appropriately selected according to purposes.

In one embodiment of the present invention, the recombinant AAV vector genome lacks the cap gene region and/or the rep gene region. In this embodiment, an AAV particle into which the recombinant AAV vector genome is packaged is not replicated alone to form an AAV particle again in an infected cell.

The second element necessary for production of AAV particles is a construct that provides proteins encoded in the wild-type AAV. The construct encodes AAV-derived genes providing AAV gene products required for formation of AAV particles. In other words, the construct comprises one or both of the major AAV ORFs, coding regions of the rep gene region and cap gene region. For production of the AAV particle of the present invention, at least a nucleic acid encoding an AAV capsid protein mutant comprising a peptide having an amino acid sequence selected from the group consisting of SEQ ID NO: 15 to SEQ ID NO: 62 is used as the cap gene. The host cell of the present invention described in above (2) which is capable of expressing the mutant can be used for production of the AAV particle. The AAV particle has a shell composed of many capsid proteins. All of the capsid proteins may be mutants, or a part of the capsid proteins may be mutants and the others may be wild-type capsid proteins. The AAV particle of the present invention may comprise one kind of a capsid protein mutant or plural kinds of a capsid protein mutants.

The rep gene of AAV is contained in coding regions of the rep gene, and includes genes encoding replication proteins Rep78, Rep68, Rep52 and Rep40. These Rep expression products are shown to possess many functions, including recognition, binding and nicking of the AAV genomic DNA replication origin, DNA helicase activity, and modulation of transcription from AAV-derived promoters.

The third element necessary for production of AAV particles is helper virus functions (also referred to as accessary functions) for AAV replication. For introduction of the helper functions, an adenovirus is generally used. However, other viruses such as herpes simplex virus type-1 or type-2, and vaccinia virus can be also used. When a virus is used, a host cell is infected with the virus as a helper virus. For example, since expression of adenovirus early genes is only required for packaging of AAV particles, an adenovirus that does not reveal expression of late genes may be used. An adenovirus mutant lacking late gene expression (for example, ts100K or ts149 adenovirus variant) can be also used. A nucleic acid construct that provides helper virus functions can be also prepared by use of nucleic acids necessary for the helper virus functions isolated from a helper virus, and then can be introduced into a host cell. The construct that provides the helper virus functions comprises a nucleotide sequence providing one or plural helper virus functions, and is provided to a host cell in the form of a plasmid, phage, transposon, cosmid, or other viruses.

For production of AAV particles, (a) a step of introducing the first element, the recombinant AAV vector genome into a host cell, (b) a step of introducing the second element, the construct that provides AAV helper functions into the host cell, and (c) a step of introducing the third element, the helper virus functions into the host cell are performed. These steps may be performed at the same time, or may be performed in order. The order of steps (a) to (c) may be any order. When the first to third elements are introduced into a host cell, the rep gene-expression products excise and replicate the recombinant vector genome. The capsid proteins expressed form a capsid, and the recombinant vector genome is packaged in the capsid to produce an AAV particle. When the host cell expresses an AAV capsid protein mutant, the shell of the AAV particle produced comprises the AAV capsid protein mutant.

The AAV particle can be isolated and purified from a culture supernatant or a lysate of the host cell by various as purification methods such CaCl density-gradient centrifugation. When a virus is used in above-described step (c), for example, a step of separating the AAV particle from the helper virus on the basis of their size may be added. The AAV particle can be also separated from the helper virus on the basis of a difference in affinity for heparin. Furthermore, the remaining helper viruses can be inactivated by known methods. For example, adenoviruses can be inactivated by heating at about 60° C., for example, for 20 minutes or more. Since AAV particles are very stable to heat, the above-described treatment is effective for selective removal of adenoviruses used as the helper virus.

(4) Method of Producing a Gene-Transduced Cell of the Present Invention

The AAV particle of the present invention obtained by above (3) is used for delivery of a heterologous polynucleotide of interest to a cell for the purpose of gene therapy or other purposes. The AAV particle is generally introduced into a cell in vivo or in vitro. For in vitro introduction, the AAV particle is brought into contact with a cell obtained from a living body. Then, the cell can be also transplanted into a living body. For introduction of the cell into a living body, the cell can be formulated as a pharmaceutical composition, and various techniques such as intramuscular, intravenous, subcutaneous and intraperitoneal administration can be used. For in vivo transduction, the AAV particle is formulated as a pharmaceutical composition, and in general, administrated parenterally (for example, administered via an intramuscular, subcutaneous, intratumor, transdermal, or intraspinal route). The pharmaceutical composition comprising the AAV particle may contain a pharmaceutically acceptable carrier and, as necessary, other agent, drug, stabilizer, carrier, adjuvant, diluent, and the like.

EXAMPLES

Hereinafter, the present invention is explained with reference to Examples which the present invention is not particularly limited to.

Example 1: Preparation of AAV2 Random Peptide Plasmid Library

Plasmid vector pAV1 (ATCC Number: 37215) carrying the genome of AAV2 was extracted from distribution host *Escherichia coli* HB101. From the extracted plasmid, a genomic of DNA AAV2 (about 4.7 kb) was excised with restriction enzyme BglII (manufactured by TAKARA BIO Inc.). This genomic DNA inserted was into pUC118 BamHI/BAP (manufactured by TAKARA BIO Inc.). The plasmid DNA thus obtained was named AAV2WG/pUC118.

The AAV2WG/pUC118 was digested with restriction enzyme ScaI (manufactured by TAKARA BIO Inc.) to obtain an about 0.8 kb fragment containing nucleotides 1190 to 2017 of the cap gene. This fragment was inserted into pUC118 HincII/BAP (manufactured by TAKARA BIO Inc.). The plasmid DNA thus obtained was named Cap-ScaI/pUC118. Then, the Cap-ScaI/pUC118 was subjected to PCR so as to perform a series of alterations in which nucleotide sequence AAC (587N) consisting of nucleotides 1759 to 1761 of the Cap gene in the Cap-ScaI/pUC118 was converted to CAG (587Q), 10 nucleotides consisting of GGC as a spacer, CAAG as a stuffer, and GCC as a spacer were inserted between nucleotide 1764 and nucleotide 1765, and nucleotide sequence CAA (5890) GCA (590A) GCT (591A) consisting of nucleotides 1765 to 1773 was converted to CAG (589Q) GCG (590A) GCC(591A), wherein the letters in brackets show amino acid numbers and the encoded amino acids. Thus, two recognition sites of restriction enzyme SfiI and the spacer, stuffer and spacer between the SfiI recognition sites were inserted. FIG. 1 shows nucleotides sequence before and after the conversion of nucleotides 1756 to 1773 of the Cap gene. The nucleotide sequence before the conversion is shown by SEQ ID NO: 1 of the sequence listing. The nucleotide sequence after the conversion is shown by SEQ ID NO: 2. The plasmid DNA comprising the converted nucleotide sequence was named Cap-ScaI-S4/pUC118. For in-fusion cloning, the Cap gene portion in the Cap-ScaI-S4/pUC118 was amplified by PCR to obtain an about 0.8 kb fragment. This fragment was used as an insert DNA.

The AAV2WG/pUC118 was subjected to PCR so that a mutation was introduced into a recognition site of restriction enzyme ScaI in an ampicillin resistant gene and a recognition site of restriction enzyme SfiI in the Rep gene, so that these recognition sites were converted to sequences that were not recognized by the restriction enzymes. For the ScaI recognition site, nucleotide sequence GAG(E) consisting of nucleotides 304 to 306 of the ampicillin resistant gene was converted to GAA(E). The sequence before the conversion is shown by SEQ ID NO: 3 and the sequence after the conversion is shown by SEQ ID NO: 4. For the SfiI recognition site, nucleotide sequence GCC(A) consisting of nucleotides 217 to 219 of the Rep gene was converted to GCA (A). The sequence before the conversion is shown by SEQ ID NO: 5 and the sequence after the conversion is shown by SEQ ID NO: 6. The plasmid DNA thus obtained was digested with ScaI (manufactured by TAKARA BIO Inc.) to obtain a linear vector lacking about 0.8 kb that was a part of the Cap gene. This was used as a linear vector for in-fusion cloning.

Using In-Fusion (registered trademark) HD cloning kit (manufactured by Clontech Laboratories, Inc.) and a cloning enhancer (manufactured by Clontech Laboratories, Inc.), the insert DNA was inserted into the linear vector, and thereby directional cloning was performed. The plasmid DNA thus obtained was named AAV2WG-Cap-ScaI-S4/pUC118Sx.

An oligo DNA (SEQ ID NO: 7) comprising a nucleotide sequence encoding a random peptide of 7 amino acids was generated by artificial synthesis. A double stranded DNA was prepared from the oligo DNA by reaction with a primer (SEQ ID NO: 8) and a Klenow Fragment (manufactured by TAKARA BIO Inc.) at 37° C. for 3 hours. The double stranded DNA was purified using a Nucleotide removal kit (manufactured by QIAGEN) and then digested with restriction enzyme BglI (manufactured by TAKARA BIO Inc.). This DNA was inserted into AAV2WG-Cap-ScaI-S4/pUC118Sx digested with SfiI, using DNA ligation kit <Mighty Mix> (manufactured by TAKARA BIO Inc.). The plasmid thus obtained was named AAV2WG-RPL/pUC118Sx, and used as an AAV2 random peptide plasmid library.

Example 2: Preparation of AAV2 Random Peptide Virus Library (1) Seeding of AAV293 Cell Cultured AAV293 cells (manufactured by Stratagene Corp.) were collected, and then suspended in DMEM (manufactured by Sigma) containing 10% FBS and 2 mM sodium L-glutamate at $5 \times 10^4$ cells/mL. Into a T225 cm² flask for cell culture (manufactured by Corning Incorporated), 40 mL of the suspension containing AAV293 cells was put and then cultured at 37° C. for 72 hours in a $CO_2$ incubator.

(2) Introduction of Plasmid into AAV293 Cell

The AAV293 cells were transfected with 400 ng of AAV2WG-RPL/pUC118Sx obtained in Example 1 and 40 μg of pHELP (manufactured by CELL BIOLABS, Inc.) by a general calcium phosphate method. Six hours after the transfection, the medium was completely removed. After 40 mL of DMEM containing 2% FBS and 2 mM sodium L-glutamate was added, the cells were cultured at 37° C. for 48 hours in a $CO_2$ incubator.

(3) Collection of AAV2 Random Peptide Virus Library

Into the T225 cm² flask being incubated, 0.5 mL of 0.5 M EDTA was added, followed by standing for several minutes. Then, the AAV293 cells were exfoliated and collected into a 50 mL tube by pipetting, and centrifuged at 300×g for 10 minutes. Then, a supernatant was removed. The cells were resuspended in 2 mL TBS (Tris-buffered saline) per flask, and then subjected thrice to sequential treatments consisting of freezing with ethanol/dry ice for 15 minutes, thawing in a 37° C. water bath for 15 minutes, and vortex for 1 minute, to collect a cell lysate containing an AAV-random peptide virus library. To the cell lysate, 5 μL of 1 M $MgCl_2$ per 1 mL of TBS and Benzonase (registered trademark) nuclease (manufactured by Merck KGaA) at a final concentration of 200 U/mL were added, followed by reaction at 37° C. for 30 minutes. Then, the reaction was terminated by an addition of 6.5 μL of 0.5 M EDTA per 1 mL of TBS. The cell lysate was centrifuged at 10000 rpm and 4° C. for 10 minutes, and then a supernatant was collected as an AAV vector solution.

(4) Titer Quantitation of AAV Vector Solution by Real-Time PCR

Into 2 μL of the AAV vector solution, 2 μL of 10× DNaseI buffer, 15.2 μL of water for injection (manufactured by Otsuka Pharmaceutical Co., Ltd.) and 0.8 μL of DNaseI (manufactured by TAKARA BIO Inc.) were added, and the mixture was incubated at 37° C. for 1 hour to remove free genomic DNAs and plasmid DNAs. For inactivation of DNaseI, the mixture was heated at 99° C. for 10 minutes. Then, 15 μL of water for injection, 4 μL of 10× ProK buffer [0.1 M Tris-HCl (pH 7.8), 0.1 M EDTA, 5% SDS] and 1 μL of Proteinase K (manufactured by TAKARA BIO Inc.) were added, and the mixture was incubated at 55° C. for an hour. Then, for inactivation of Proteinase K, the mixture was heated at 95° C. for 10 minutes. This sample was subjected to AAV titer quantitation using SYBR (registered trademark) Premix ExTaq2 (manufactured by TAKARA BIO Inc.) and primers (SEQ ID NO: 9 and SEQ ID NO: 10) according to instructions attached to a kit. The sample was diluted 50-fold with water for injection, and 2 μL of the diluted solution was used for titer quantitation. As a standard, a linear DNA obtained by restriction enzyme digestion of pAV1 was used.

Example 3: Purification of AAV Random Peptide Virus Library (1) Purification 1 by Cesium Chloride Density-Gradient Centrifugation In a 40 PA tube for ultracentrifugation (manufactured by HITACHI-KOKI Co., Ltd.), 4 mL of a cesium chloride solution adjusted to a density of 1.5, 4 mL of a cesium chloride solution adjusted to a density of 1.25, and 28 mL of the AAV vector solution prepared in Example 2-(4) were layered in this order from the bottom. The tube was centrifuged at 25000 rpm and 16° C. for 3 hours by ultracentrifuge HIMAC (manufactured by HITACHI-KOKI Co., Ltd.). After centrifugation, 28 mL of the solution was removed from the top of the tube, and then, an aliquot of 0.7 mL of the solution was subsequently collected from the top into a 1.5 mL tube. In the same manner as Example 2-(4), titer of the AAV vector contained in each collected solution was quantitated.

(2) Purification 2 by Cesium Chloride Density-Gradient Centrifugation

In several fractions that were shown to have high titer in Example 3-(1), a cesium chloride solution adjusted to a density of 1.39 was added to reach a total volume of 10.5 mL. The solution thus obtained was put in a 13PA tube for ultracentrifugation (manufactured by HITACHI-KOKI Co., Ltd.), and then centrifuged at 38000 rpm and 18° C. for 16 hours. After centrifugation, an aliquot of 0.7 mL of the solution was successively collected from the top of the tube.

In the same manner as Example 2-(4), titer of the AAV vector contained in each collected solution was quantitated.

(3) Desalting by Dialysis

Several fractions that were shown to have high titer in Example 3-(2) were mixed and then added to a Slide-A-lyzer dialysis cassette (manufactured by Pierce). The purified AAV solution was desalted by dialysis with 1 L of phosphate buffered saline (PBS) at 4° C. for 3 hours twice and dialysis with 500 mL of a PBS/5% sorbitol solution at 4° C. overnight. Then, the solution was collected, sterilized with a 0.22 μm filter (manufactured by Millipore), and stored at −80° C. until just before use. Separately, titer of the purified AAV particles was quantitated in the same manner as Example 2-(4).

Example 4: Screening of AAV2 Random Peptide Library (1) Tail Vein Administration to Mouse The purified AAV particles obtained in Example 3-(3) were administered to BALB/c mice via a tail vein at 1.5× $10^{14}$ viral genome (VG)/kg. After 72 hours from the administration, brains were collected, and genomic DNAs were extracted by use of NucleoSpin (registered trademark) tissue (manufacture by MACHEREY-NAGEL GmbH & Co. KG) (Round 1).

(2) Recloning of Random Peptide Sequence by PCR

A DNA encoding the random peptide sequence was amplified using the genomic DNA extracted in Example 4-(1) as a template, and PrimeSTAR (registered trademark) GXL DNA polymerase (manufactured by TAKARA BIO Inc.). As primers, forward primer 1 (SEQ ID NO: 11) and reverse primer 1 (SEQ ID NO: 12) were used. PCR was performed by repeated 30 cycles and each cycle of PCR consisted of 98° C. for 10 seconds, 55° C. for 15 seconds, and 68° C. for 40 seconds. Then, a twenty-fifth part of the PCR reaction solution, forward primer 2 (SEQ ID NO: 13) and reverse primer 2 (SEQ ID NO: 14) were used to prepare a reaction mixture in the same amount as before. The reaction mixture was subjected to PCR with 30 cycles, in which each cycle consisted of 98° C. for 10 seconds, 55° C. for 15 seconds, and 68° C. for 15 seconds. From the reaction solution thus obtained, a DNA was purified by use of Nucleospin extract II (manufacture by MACHEREY-NAGEL GmbH & Co. KG), and digested with restriction enzyme BglI. After electrophoresis, a digested product was purified by use of Nucleospin extract II, and recloned into AAV2WG-Cap-ScaI-S4/pUC118Sx as prepared in Example 1 by use of DNA ligation kit <Mighty Mix>.

(3) Production and Purification of AAV2 Random Peptide Virus Library

Production of an AAV2 random peptide virus library and purification of AAV particles were performed using the plasmid obtained in Example 4-(2) by the same methods as those described in Example 2 and Example 3.

(4) Screening

In the same manner as Example 4-(1), screening (administration of AAV particles to mice and collection of brains) was performed and genomic DNAs were extracted (Round 2). Furthermore, using the extracted genomic DNA, recloning, production and purification of a library, and screening were performed again, and genomic DNAs were extracted (Round 3).

(5) Sequencing of Random Peptide

At each screening stage (Round 1 to Round 3), sequencing of the AAV random peptide plasmid library was performed. Peptide sequences encoded by clones that accumulated in the brain at round 2 and round 3 and the appearance frequency are shown in Table 1 and Table 2.

TABLE 1

| Sequence | SEQ ID NO: | Round 2 | Round 3 |
|---|---|---|---|
| GSGVTWV | 15 | 8 | 4 |
| AHGYREP | 16 | 4 | 2 |
| EYGFREG | 17 | 16 | 1 |
| ETGHGWV | 18 | 4 | 1 |
| GGGIGYV | 19 | 14 | — |
| ERGVGWV | 20 | 5 | — |
| ENGVGWV | 21 | 2 | — |
| GSGVGWV | 22 | 2 | — |
| ADGITWG | 23 | 1 | — |
| ADGTRWV | 24 | 1 | — |
| ADKVGWV | 25 | 1 | — |
| AGGVGWT | 26 | 1 | — |
| AGGVTGV | 27 | 1 | — |
| AGNAGGM | 28 | 1 | — |
| AGQLGWV | 29 | 1 | — |
| ARGTEWE | 30 | 1 | — |
| DAGHGFV | 31 | 1 | — |
| EANVGWV | 32 | 1 | — |
| ECGLGEG | 33 | 1 | — |
| EGEVTWL | 34 | 1 | — |
| EGGDGRV | 35 | 1 | — |
| EGGFGEA | 36 | 1 | — |
| EGGG | 37 | 1 | — |
| EGGMVWV | 38 | 1 | — |
| EGGVGWT | 39 | 1 | — |
| EGGVMWL | 40 | 1 | — |

TABLE 2

| Sequence | SEQ ID NO: | Round 2 | Round 3 |
|---|---|---|---|
| EGQVTWL | 41 | 1 | — |
| ERGHGWG | 42 | 1 | — |
| ESGVGWK | 43 | 1 | — |
| GDGFGGV | 44 | 1 | — |
| GDGVTWA | 45 | 1 | — |
| GEGRGWV | 46 | 1 | — |
| GGGDGWI | 47 | 1 | — |

TABLE 2-continued

| Sequence | SEQ ID NO: | Round 2 | Round 3 |
|---|---|---|---|
| GGGDSWV | 48 | 1 | – |
| GGGIAWVAQAAL | 49 | 1 | – |
| GGGVGWA | 50 | 1 | – |
| GKGQVME | 51 | 1 | – |
| GNGTGGG | 52 | 1 | – |
| GQGGHME | 53 | 1 | – |
| GRGVTWV | 54 | 1 | – |
| GSGMGWV | 55 | 1 | – |
| GVGGGVV | 56 | 1 | – |
| NDVRGRV | 57 | 1 | – |
| RDGLGFV | 58 | 1 | – |
| TDGLGWV | 59 | 1 | – |
| TEGHGWV | 60 | 1 | – |
| VAERLYG | 61 | 1 | – |
| VARGAGE | 62 | 1 | – |
| Total | | 95 | 8 |

As shown in Table 1 and Table 2, AAV having capsids comprising the specific peptide sequences accumulated in the brain. In particular, it is suggested that peptide sequences GSGVTWV (SEQ ID NO: 15), AHGYREP (SEQ ID NO: 16), EYGFREG (SEQ ID NO: 17) and ETGHGWV (SEQ ID NO: 18) which were observed at round 3 tend to infect the brain.

In addition, it is suggested that the peptide sequences of SEQ ID NO: 63 to SEQ ID NO: 110, which are sequences comprising the sequences observed at round 2 and a spacer, tend to infect the brain. In particular, GGSGVTWVA (SEQ ID NO: 63), GAHGYREPA (SEQ ID NO: 64), GEYGFREGA (SEQ ID NO: (SEQ ID NO: 66), which are sequences 65) and GETGHGWVA comprising the sequences observed at round 3 and a spacer, tend to infect the brain.

Example 5: Evaluation of Tropism of AAV Vector Having Acquired Peptide Sequence (1) Construction of pRC-GDDGTRG Having Acquired Peptide Sequence The AAV2WG-Cap-ScaI-S4/pUC118Sx clones having the peptide sequences (SEQ ID NOs: 15-20) as obtained in Example 4-(5) were digested with restriction enzymes SnaBI (manufactured by TAKARA BIO Inc.) and HindIII (manufactured by TAKARA BIO Inc.) to obtain a fragment. The fragment was ligated to a vector fragment obtained by digestion of a pAAVRC2 vector (manufactured by CELL BIOLABS, Inc.) with SnaBI and HindIII DNA by ligation kit <Mighty Mix> (manufactured by TAKARA BIO Inc.) to obtain helper plasmids pRC-GSGVTWV, pRC-AHGYREP, pRC-EYGFREG, pRC-ETGHGWV, pRC-GGGIGYV, and pRC-ERGVGWV.

(2) Production and Purification of AAV2-LacZ Capsid Mutant

Using PEIpro® (transfection reagent manufactured by Polyplus Transfection), 293 T cells seeded on a T255 cm$^2$ flask were transfected with pAAV-LacZ (manufactured by TAKARA BIO Inc.), pHELP, and the pRC helper plasmid (pRC-GSGVTWV, pRC-AHGYREP, pRC-EYGFREG, pRC-ETGHGWV, pRC-GGGIGYV, or pRC-ERGVGWV) prepared in Example 5-(1). As a control, transfection with a pRC2 vector carrying the wild-type capsid instead of the pRC helper plasmid having the peptide sequence was performed. The transfected 293 T cells were cultured at 37° C. for 72 hours in a $CO_2$ incubator. A supernatant containing AAV was collected from the T255 cm$^2$ flask, and then subjected to affinity purification using AVB sepharose (manufactured by GE healthcare). Then, AAV was concentrated and purified by ultrafiltration to prepare a purified AAV solution. Then, titer of the AAV vectors was quantitated by the method described in Example 2-(4).

(3) Administration of Purified AAV Solution to Mouse

The purified AAV solution obtained in Example 5-(2) was filtered using a 0.22 μm filter, and then administered to mice via a tail vein at 0.5×10$^{11}$ VG/mouse.

(4) Preparation of Genomic DNA from Brain and Other Tissues And Quantitation of AAV Genome The mice to which AAV was administered in Example 5-(3) were euthanized 4 weeks after administration, and each tissue was collected. A genomic DNA was extracted from each tissue by use of NucleoSpin® tissue (extraction kit manufactured by MACHEREY-NAGEL GmbH & Co. KG). The extracted genomic DNA as a sample was subjected to real-time PCR to determine the amount of the AAV vector genome contained in each tissue. FIG. 2 shows the number of AAV genomic DNA molecules per 1 μg of the total genomic DNA in each tissue.

As can be seen from FIG. 2, the AAV vectors comprising the capsids having peptide sequences GSGVTWV, AHGYREP, EYGFREG, ETGHGWV, GGGIGYV, and ERGVGWV tended to transfer into the brain. Further, some of the AAV vectors had tropism for lung as well as brain.

INDUSTRIAL APPLICABILITY

According to the present invention, AAV capsid protein mutants having tropism for brain via systemic administration, and their amino acid sequences are provided, and thus, a method of efficiently introducing a gene into a brain is provided.

SEQUENCE LISTING FREE TEXT

SEQ ID NO:1: AAV2 capsid 586-591 coding sequence
SEQ ID NO: 2: Converted AAV2 capsid coding sequence
SEQ ID NO: 3: Ampicillin resistance gene before conversion
SEQ ID NO: 4: Ampicillin resistance gene after conversion
SEQ ID NO: 5: AAV2 rep gene before conversion
SEQ ID NO: 6: AAV2 rep gene after conversion
SEQ ID NO: 7: DNA sequence coding random peptide
SEQ ID NO: 8: Primer for synthesizing double strand DNA
SEQ ID NO: 9: Forward primer for quantitation of AAV titer
SEQ ID NO:10: Reverse primer for quantitation of AAV titer
SEQ ID NO: 11: Forward primer1 for amplification of random peptide coding region SEQ ID NO: 12: Reverse primer1 for amplification of random peptide coding region
SEQ ID NO: 13: Forward primer2 for amplification of random peptide coding region
SEQ ID NO: 14: Reverse primer2 for amplification of random peptide coding region
SEQ ID NO: 15: Peptide sequence GSGVTWV for AAV capsid protein mutant
SEQ ID NO: 16: Peptide sequence AHGYREP for AAV capsid protein mutant
SEQ ID NO: 17: Peptide sequence EYGFREG for AAV capsid protein mutant
SEQ ID NO: 18: Peptide sequence ETGHGWV for AAV capsid protein mutant
SEQ ID NO: 19: Peptide sequence GGGIGYV for AAV capsid protein mutant
SEQ ID NO: 20: Peptide sequence ERGVGWV for AAV capsid protein mutant
SEQ ID NO: 21: Peptide sequence ENGVGWV for AAV capsid protein mutant
SEQ ID NO: 22: Peptide sequence GSGVGWV for AAV capsid protein mutant
SEQ ID NO: 23: Peptide sequence ADGITWG for AAV capsid protein mutant
SEQ ID NO: 24: Peptide sequence ADGTRWV for AAV capsid protein mutant
SEQ ID NO: 25: Peptide sequence ADKVGWV for AAV capsid protein mutant
SEQ ID NO: 26: Peptide sequence AGGVGWT for AAV capsid protein mutant
SEQ ID NO: 27: Peptide sequence AGGVTGV for AAV capsid protein mutant
SEQ ID NO: 28: Peptide sequence AGNAGGM for AAV capsid protein mutant
SEQ ID NO: 29: Peptide sequence AGQLGWV for AAV capsid protein mutant
SEQ ID NO: 30: Peptide sequence ARGTEWE for AAV capsid protein mutant
SEQ ID NO: 31: Peptide sequence DAGHGFV for AAV capsid protein mutant
SEQ ID NO: 32: Peptide sequence EANVGWV for AAV capsid protein mutant
SEQ ID NO: 33: Peptide sequence ECGLGEG for AAV capsid protein mutant
SEQ ID NO: 34: Peptide sequence EGEVTWL for AAV capsid protein mutant
SEQ ID NO: 35: Peptide sequence EGGDGRV for AAV capsid protein mutant
SEQ ID NO: 36: Peptide sequence EGGFGEA for AAV capsid protein mutant
SEQ ID NO: 37: Peptide sequence EGGG for AAV capsid protein mutant
SEQ ID NO: 38: Peptide sequence EGGMVWV for AAV capsid protein mutant
SEQ ID NO: 39: Peptide sequence EGGVGWT for AAV capsid protein mutant
SEQ ID NO: 40: Peptide sequence EGGVMWL for AAV capsid protein mutant
SEQ ID NO: 41: Peptide sequence EGQVTWL for AAV capsid protein mutant
SEQ ID NO: 42: Peptide sequence ERGHGWG for AAV capsid protein mutant
SEQ ID NO: 43: Peptide sequence ESGVGWK for AAV capsid protein mutant
SEQ ID NO: 44: Peptide sequence GDGFGGV for AAV capsid protein mutant
SEQ ID NO: 45: Peptide sequence GDGVTWA for AAV capsid protein mutant
SEQ ID NO: 46: Peptide sequence GEGRGWV for AAV capsid protein mutant
SEQ ID NO: 47: Peptide sequence GGGDGWI for AAV capsid protein mutant
SEQ ID NO: 48: Peptide sequence GGGDSWV for AAV capsid protein mutant
SEQ ID NO: 49: Peptide sequence GGGIAWVAQAAL for AAV capsid protein mutant
SEQ ID NO: 50: Peptide sequence GGGVGWA for AAV capsid protein mutant
SEQ ID NO: 51: Peptide sequence GKGOVME for AAV capsid protein mutant
SEQ ID NO: 52: Peptide sequence GNGTGGG for AAV capsid protein mutant
SEQ ID NO: 53: Peptide sequence GOGGHME for AAV capsid protein mutant
SEQ ID NO: 54: Peptide sequence GRGVTWV for AAV capsid protein mutant
SEQ ID NO: 55: Peptide sequence GSGMGWV for AAV capsid protein mutant
SEQ ID NO: 56: Peptide sequence GVGGGVV for AAV capsid protein mutant
SEQ ID NO: 57: Peptide sequence NDVRGRV for AAV capsid protein mutant
SEQ ID NO: 58: Peptide sequence RDGLGFV for AAV capsid protein mutant
SEQ ID NO: 59: Peptide sequence TDGLGWV for AAV capsid protein mutant
SEQ ID NO: 60: Peptide sequence TEGHGWV for AAV capsid protein mutant
SEQ ID NO: 61: Peptide sequence VAERLYG for AAV capsid protein mutant
SEQ ID NO: 62: Peptide sequence VARGAGE for AAV capsid protein mutant
SEQ ID NO: 63: Peptide sequence GGSGVTWVA for AAV capsid protein mutant
SEQ ID NO: 64: Peptide sequence GAHGYREPA for AAV capsid protein mutant
SEQ ID NO: 65: Peptide sequence GEYGFREGA for AAV capsid protein mutant
SEQ ID NO: 66: Peptide sequence GETGHGWVA for AAV capsid protein mutant
SEQ ID NO: 67: Peptide sequence GGGGIGYVA for AAV capsid protein mutant
SEQ ID NO: 68: Peptide sequence GERGVGWVA for AAV capsid protein mutant
SEQ ID NO: 69: Peptide sequence GENGVGWVA for AAV capsid protein mutant
SEQ ID NO: 70: Peptide sequence GGSGVGWVA for AAV capsid protein mutant
SEQ ID NO: 71: Peptide sequence GADGITWGA for AAV capsid protein mutant
SEQ ID NO: 72: Peptide sequence GADGTRWVA for AAV capsid protein mutant
SEQ ID NO: 73: Peptide sequence GADKVGWVA for AAV capsid protein mutant
SEQ ID NO: 74: Peptide sequence GAGGVGWTA for AAV capsid protein mutant
SEQ ID NO: 75: Peptide sequence GAGGVTGVA for AAV capsid protein mutant
SEQ ID NO: 76: Peptide sequence GAGNAGGMA for AAV capsid protein mutant
SEQ ID NO: 77: Peptide sequence GAGOLGWVA for AAV capsid protein mutant SEQ ID NO: 78: Peptide sequence GARGTEWEA for AAV capsid protein mutant
SEQ ID NO: 79: Peptide sequence GDAGHGEVA for AAV capsid protein mutant
SEQ ID NO: 80: Peptide sequence GEANVGWVA for AAV capsid protein mutant
SEQ ID NO: 81: Peptide sequence GECGLGEGA for AAV capsid protein mutant
SEQ ID NO: 82: Peptide sequence GEGEVTWLA for AAV capsid protein mutant
SEQ ID NO: 83: Peptide sequence GEGGDGRVA for AAV capsid protein mutant
SEQ ID NO: 84: Peptide sequence GEGGFGEAA for AAV capsid protein mutant
SEQ ID NO: 85: Peptide sequence GEGGGA for AAV capsid protein mutant
SEQ ID NO: 86: Peptide sequence GEGGMVWVA for AAV capsid protein mutant
SEQ ID NO: 87: Peptide sequence GEGGVGWTA for AAV capsid protein mutant
SEQ ID NO: 88: Peptide sequence GEGGVMWLA for AAV capsid protein mutant
SEQ ID NO: 89: Peptide sequence GEGQVTWLA for AAV capsid protein mutant
SEQ ID NO: 90: Peptide sequence GERGHGWGA for AAV capsid protein mutant
SEQ ID NO: 91: Peptide sequence GESGVGWKA for AAV capsid protein mutant
SEQ ID NO: 92: Peptide sequence GGDGFGGVA for AAV capsid protein mutant
SEQ ID NO: 93: Peptide sequence GGDGVTWAA for AAV capsid protein mutant
SEQ ID NO: 94: Peptide sequence GGEGRGWVA for AAV capsid protein mutant
SEQ ID NO: 95: Peptide sequence GGGGDGWIA for AAV capsid protein mutant
SEQ ID NO: 96: Peptide sequence GGGGDSWVA for AAV capsid protein mutant
SEQ ID NO: 97: Peptide sequence GGGGIAWVAQAALA for AAV capsid protein mutant
SEQ ID NO: 98: Peptide sequence GGGGVGWAA for AAV capsid protein mutant
SEQ ID NO: 99: Peptide sequence GGKGQVMEA for AAV capsid protein mutant
SEQ ID NO: 100: Peptide sequence GGNGTGGGA for AAV capsid protein mutant
SEQ ID NO:101: Peptide sequence GGOGGHMEA for AAV capsid protein mutant
SEQ ID NO:102: Peptide sequence GGRGVTWVA for AAV capsid protein mutant
SEQ ID NO:103: Peptide sequence GGSGMGWVA for AAV capsid protein mutant
SEQ ID NO:104: Peptide sequence GGVGGGVVA for AAV capsid protein mutant
SEQ ID NO: 105: Peptide sequence GNDVRGRVA for AAV capsid protein mutant
SEQ ID NO:106: Peptide sequence GRDGLGEVA for AAV capsid protein mutant
SEQ ID NO: 107: Peptide sequence GTDGLGWVA for AAV capsid protein mutant
SEQ ID NO: 108: Peptide sequence GTEGHGWVA for AAV capsid protein mutant
SEQ ID NO: 109: Peptide sequence GVAERLYGA for AAV capsid protein mutant
SEQ ID NO: 110: Peptide sequence GVARGAGEA for AAV capsid protein mutant
SEQ ID NO: 111: Peptide sequence represented by Formula I
SEQ ID NO: 112: Peptide sequence represented by Formula II
SEQ ID NO: 113: Peptide sequence represented by Formula III
SEQ ID NO: 114: Peptide sequence represented by Formula IV
SEQ ID NO: 115: Peptide sequence represented by Formula V
SEQ ID NO:116: Peptide sequence represented by Formula VI

The invention claimed is:

1. A nucleic acid encoding a mutant of an adeno-associated virus-2 (AAV-2) capsid protein comprising a peptide, wherein the peptide consists of the amino acid sequence of SEQ ID NO: 18 or SEQ ID NO: 66, and wherein the peptide is placed at a position between amino acids corresponding to amino acid number 588 and amino acid number 589 of AAV2 VP1 in the AAV capsid protein and wherein the mutant AAV-2 capsid protein has cellular tropism for the brain and/or lungs.

2. A recombinant DNA comprising the nucleic acid according to claim 1.

3. An in vitro cell comprising the nucleic acid according to claim 1.

4. An AAV particle comprising a mutant of an AAV-2 capsid protein comprising a peptide wherein the peptide consists of the amino acid sequence of SEQ ID NO: 18 or SEQ ID NO: 66, and wherein the peptide is placed at a position between amino acids corresponding to amino acid number 588 and amino acid number 589 of AAV2 VP1 in the AAV capsid protein and wherein the mutant AAV-2 capsid protein has cellular tropism for the brain and/or lungs.

5. An in vitro cell comprising the recombinant DNA according to claim 2.

* * * * *

SEQUENCE LISTING

<160> NUMBER OF SEQ ID NOS: 116

<210> SEQ ID NO 1
<211> LENGTH: 18
<212> TYPE: DNA
<213> ORGANISM: Artificial Sequence
<220> FEATURE:
<223> OTHER INFORMATION: AAV2 capsid 586-591 coding sequence

<400> SEQUENCE: 1
gccaacagac aagcagct                                                18

<210> SEQ ID NO 2
<211> LENGTH: 28
<212> TYPE: DNA
<213> ORGANISM: Artificial Sequence
<220> FEATURE:
<223> OTHER INFORMATION: Converted AAV2 capsid coding sequence

<400> SEQUENCE: 2
ggccagagag gccaaggccc aggcggcc                                      28

<210> SEQ ID NO 3
<211> LENGTH: 45

```
<212> TYPE: DNA
<213> ORGANISM: Artificial Sequence
<220> FEATURE:
<223> OTHER INFORMATION: Ampicillin resistance gene before conversion

<400> SEQUENCE: 3
tattctcaga atgacttggt tgagtactca ccagtcacag aaaag          45

<210> SEQ ID NO 4
<211> LENGTH: 45
<212> TYPE: DNA
<213> ORGANISM: Artificial Sequence
<220> FEATURE:
<223> OTHER INFORMATION: Ampicillin resistance gene after conversion

<400> SEQUENCE: 4
tattctcaga atgacttggt tgaatactca ccagtcacag aaaag          45

<210> SEQ ID NO 5
<211> LENGTH: 45
<212> TYPE: DNA
<213> ORGANISM: Artificial Sequence
<220> FEATURE:
<223> OTHER INFORMATION: AAV2 rep gene before conversion

<400> SEQUENCE: 5
gaatggcgcc gtgtgagtaa ggccccggag gccctttttct ttgtg          45

<210> SEQ ID NO 6
<211> LENGTH: 45
<212> TYPE: DNA
<213> ORGANISM: Artificial Sequence
<220> FEATURE:
<223> OTHER INFORMATION: AAV2 rep gene after conversion

<400> SEQUENCE: 6
gaatggcgcc gtgtgagtaa ggccccggag gccctttttct ttgtg          45

<210> SEQ ID NO 7
<211> LENGTH: 56
<212> TYPE: DNA
<213> ORGANISM: Artificial Sequence
<220> FEATURE:
<223> OTHER INFORMATION: DNA sequence coding random peptide
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
```

```
<223> OTHER INFORMATION: n is a, c, g, or t

<400> SEQUENCE: 7
cagtcggcca gagaggcnnk nnknnknnkn nknnknnkgc ccaggcggct gacgag        56

<210> SEQ ID NO 8
<211> LENGTH: 16
<212> TYPE: DNA
<213> ORGANISM: Artificial Sequence
<220> FEATURE:
<223> OTHER INFORMATION: Primer for synthesizing double strand DNA

<400> SEQUENCE: 8
ctcgtcagcc gcctgg                                                    16

<210> SEQ ID NO 9
<211> LENGTH: 20
<212> TYPE: DNA
<213> ORGANISM: Artificial Sequence
<220> FEATURE:
<223> OTHER INFORMATION: Forward primer for quantitation of AAV titer

<400> SEQUENCE: 9
atcatatgcc aagtacgccc                                                20

<210> SEQ ID NO 10
<211> LENGTH: 19
<212> TYPE: DNA
<213> ORGANISM: Artificial Sequence
<220> FEATURE:
<223> OTHER INFORMATION: Reverse primer for quantitation of AAV titer

<400> SEQUENCE: 10
ccaaaaccgc atcaccatg                                                 19

<210> SEQ ID NO 11
<211> LENGTH: 19
<212> TYPE: DNA
<213> ORGANISM: Artificial Sequence
<220> FEATURE:
<223> OTHER INFORMATION: Forward primer1 for amplification of random
      peptide coding region

<400> SEQUENCE: 11
ccaaaaccgc atcaccatg                                                 19

<210> SEQ ID NO 12
<211> LENGTH: 22
<212> TYPE: DNA
<213> ORGANISM: Artificial Sequence
<220> FEATURE:
<223> OTHER INFORMATION: Reverse primer1 for amplification of random
      peptide coding region

<400> SEQUENCE: 12
ctgtcccgtg gagtactgtg tg                                             22

<210> SEQ ID NO 13
<211> LENGTH: 22
<212> TYPE: DNA
<213> ORGANISM: Artificial Sequence
<220> FEATURE:
<223> OTHER INFORMATION: Forward primer2 for amplification of random
      peptide coding region

<400> SEQUENCE: 13
```

```
ctgtcccgtg gagtactgtg tg                                              22
```

<210> SEQ ID NO 14
<211> LENGTH: 23
<212> TYPE: DNA
<213> ORGANISM: Artificial Sequence
<220> FEATURE:
<223> OTHER INFORMATION: Reverse primer2 for amplification of random
      peptide coding region

<400> SEQUENCE: 14

```
gcccctgaag gtacacatct ctg                                             23
```

<210> SEQ ID NO 15
<211> LENGTH: 7
<212> TYPE: PRT
<213> ORGANISM: Artificial Sequence
<220> FEATURE:
<223> OTHER INFORMATION: Peptide sequence GSGVTWV for AAV capsid protein
      mutant

<400> SEQUENCE: 15

Gly Ser Gly Val Thr Trp Val
1               5

<210> SEQ ID NO 16
<211> LENGTH: 7
<212> TYPE: PRT
<213> ORGANISM: Artificial Sequence
<220> FEATURE:
<223> OTHER INFORMATION: Peptide sequence AHGYREP for AAV capsid protein
      mutant

<400> SEQUENCE: 16

Ala His Gly Tyr Arg Glu Pro
1               5

<210> SEQ ID NO 17
<211> LENGTH: 7
<212> TYPE: PRT
<213> ORGANISM: Artificial Sequence
<220> FEATURE:
<223> OTHER INFORMATION: Peptide sequence EYGFREG for AAV capsid protein
      mutant

<400> SEQUENCE: 17

Glu Tyr Gly Phe Arg Glu Gly
1               5

<210> SEQ ID NO 18
<211> LENGTH: 7
<212> TYPE: PRT
<213> ORGANISM: Artificial Sequence
<220> FEATURE:
<223> OTHER INFORMATION: Peptide sequence ETGHGWV for AAV capsid protein
      mutant

<400> SEQUENCE: 18

Glu Thr Gly His Gly Trp Val
1               5

<210> SEQ ID NO 19
<211> LENGTH: 7
<212> TYPE: PRT
<213> ORGANISM: Artificial Sequence
<220> FEATURE:
<223> OTHER INFORMATION: Peptide sequence GGGIGYV for AAV capsid protein
      mutant -continued

```
<400> SEQUENCE: 19

Gly Gly Gly Ile Gly Tyr Val
1               5

<210> SEQ ID NO 20
<211> LENGTH: 7
<212> TYPE: PRT
<213> ORGANISM: Artificial Sequence
<220> FEATURE:
<223> OTHER INFORMATION: Peptide sequence ERGVGWV for AAV capsid protein
      mutant

<400> SEQUENCE: 20

Glu Arg Gly Val Gly Trp Val
1               5

<210> SEQ ID NO 21
<211> LENGTH: 7
<212> TYPE: PRT
<213> ORGANISM: Artificial Sequence
<220> FEATURE:
<223> OTHER INFORMATION: Peptide sequence ENGVGWV for AAV capsid protein
      mutant

<400> SEQUENCE: 21

Glu Asn Gly Val Gly Trp Val
1               5

<210> SEQ ID NO 22
<211> LENGTH: 7
<212> TYPE: PRT
<213> ORGANISM: Artificial Sequence
<220> FEATURE:
<223> OTHER INFORMATION: Peptide sequence GSGVGWV for AAV capsid protein
      mutant

<400> SEQUENCE: 22

Gly Ser Gly Val Gly Trp Val
1               5

<210> SEQ ID NO 23
<211> LENGTH: 7
<212> TYPE: PRT
<213> ORGANISM: Artificial Sequence
<220> FEATURE:
<223> OTHER INFORMATION: Peptide sequence ADGITWG for AAV capsid protein
      mutant

<400> SEQUENCE: 23

Ala Asp Gly Ile Thr Trp Gly
1               5

<210> SEQ ID NO 24
<211> LENGTH: 7
<212> TYPE: PRT
<213> ORGANISM: Artificial Sequence
<220> FEATURE:
<223> OTHER INFORMATION: Peptide sequence ADGTRWV for AAV capsid protein
      mutant

<400> SEQUENCE: 24

Ala Asp Gly Thr Arg Trp Val
1               5

<210> SEQ ID NO 25
<211> LENGTH: 7
```

```
<212> TYPE: PRT
<213> ORGANISM: Artificial Sequence
<220> FEATURE:
<223> OTHER INFORMATION: Peptide sequence ADKVGWV for AAV capsid protein
      mutant

<400> SEQUENCE: 25

Ala Asp Lys Val Gly Trp Val
1               5

<210> SEQ ID NO 26
<211> LENGTH: 7
<212> TYPE: PRT
<213> ORGANISM: Artificial Sequence
<220> FEATURE:
<223> OTHER INFORMATION: Peptide sequence AGGVGWT for AAV capsid protein
      mutant

<400> SEQUENCE: 26

Ala Gly Gly Val Gly Trp Thr
1               5

<210> SEQ ID NO 27
<211> LENGTH: 7
<212> TYPE: PRT
<213> ORGANISM: Artificial Sequence
<220> FEATURE:
<223> OTHER INFORMATION: Peptide sequence AGGVTGV for AAV capsid protein
      mutant

<400> SEQUENCE: 27

Ala Gly Gly Val Thr Gly Val
1               5

<210> SEQ ID NO 28
<211> LENGTH: 7
<212> TYPE: PRT
<213> ORGANISM: Artificial Sequence
<220> FEATURE:
<223> OTHER INFORMATION: Peptide sequence AGNAGGM for AAV capsid protein
      mutant

<400> SEQUENCE: 28

Ala Gly Asn Ala Gly Gly Met
1               5

<210> SEQ ID NO 29
<211> LENGTH: 7
<212> TYPE: PRT
<213> ORGANISM: Artificial Sequence
<220> FEATURE:
<223> OTHER INFORMATION: Peptide sequence AGQLGWV for AAV capsid protein
      mutant

<400> SEQUENCE: 29

Ala Gly Gln Leu Gly Trp Val
1               5

<210> SEQ ID NO 30
<211> LENGTH: 7
<212> TYPE: PRT
<213> ORGANISM: Artificial Sequence
<220> FEATURE:
<223> OTHER INFORMATION: Peptide sequence ARGTEWE for AAV capsid protein
      mutant

<400> SEQUENCE: 30

Ala Arg Gly Thr Glu Trp Glu
```

```
<210> SEQ ID NO 31
<211> LENGTH: 7
<212> TYPE: PRT
<213> ORGANISM: Artificial Sequence
<220> FEATURE:
<223> OTHER INFORMATION: Peptide sequence DAGHGFV for AAV capsid protein
      mutant

<400> SEQUENCE: 31

Asp Ala Gly His Gly Phe Val
1               5

<210> SEQ ID NO 32
<211> LENGTH: 7
<212> TYPE: PRT
<213> ORGANISM: Artificial Sequence
<220> FEATURE:
<223> OTHER INFORMATION: Peptide sequence EANVGWV for AAV capsid protein
      mutant

<400> SEQUENCE: 32

Glu Ala Asn Val Gly Trp Val
1               5

<210> SEQ ID NO 33
<211> LENGTH: 7
<212> TYPE: PRT
<213> ORGANISM: Artificial Sequence
<220> FEATURE:
<223> OTHER INFORMATION: Peptide sequence ECGLGEG for AAV capsid protein
      mutant

<400> SEQUENCE: 33

Glu Cys Gly Leu Gly Glu Gly
1               5

<210> SEQ ID NO 34
<211> LENGTH: 7
<212> TYPE: PRT
<213> ORGANISM: Artificial Sequence
<220> FEATURE:
<223> OTHER INFORMATION: Peptide sequence EGEVTWL for AAV capsid protein
      mutant

<400> SEQUENCE: 34

Glu Gly Glu Val Thr Trp Leu
1               5

<210> SEQ ID NO 35
<211> LENGTH: 7
<212> TYPE: PRT
<213> ORGANISM: Artificial Sequence
<220> FEATURE:
<223> OTHER INFORMATION: Peptide sequence EGGDGRV for AAV capsid protein
      mutant

<400> SEQUENCE: 35

Glu Gly Gly Asp Gly Arg Val
1               5

<210> SEQ ID NO 36
<211> LENGTH: 7
<212> TYPE: PRT
<213> ORGANISM: Artificial Sequence
<220> FEATURE:
<223> OTHER INFORMATION: Peptide sequence EGGFGEA for AAV capsid protein
```

```
                                mutant

<400> SEQUENCE: 36

Glu Gly Gly Phe Gly Glu Ala
1               5

<210> SEQ ID NO 37
<211> LENGTH: 4
<212> TYPE: PRT
<213> ORGANISM: Artificial Sequence
<220> FEATURE:
<223> OTHER INFORMATION: Peptide sequence EGGG for AAV capsid protein
      mutant

<400> SEQUENCE: 37

Glu Gly Gly Gly
1

<210> SEQ ID NO 38
<211> LENGTH: 7
<212> TYPE: PRT
<213> ORGANISM: Artificial Sequence
<220> FEATURE:
<223> OTHER INFORMATION: Peptide sequence EGGMVWV for AAV capsid protein
      mutant

<400> SEQUENCE: 38

Glu Gly Gly Met Val Trp Val
1               5

<210> SEQ ID NO 39
<211> LENGTH: 7
<212> TYPE: PRT
<213> ORGANISM: Artificial Sequence
<220> FEATURE:
<223> OTHER INFORMATION: Peptide sequence EGGVGWT for AAV capsid protein
      mutant

<400> SEQUENCE: 39

Glu Gly Gly Val Gly Trp Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Peptide sequence EGGVMWL for AAV capsid protein
      mutant

<400> SEQUENCE: 40

Glu Gly Gly Val Met Trp Leu
1               5

<210> SEQ ID NO 41
<211> LENGTH: 7
<212> TYPE: PRT
<213> ORGANISM: Artificial Sequence
<220> FEATURE:
<223> OTHER INFORMATION: Peptide sequence EGQVTWL for AAV capsid protein
      mutant

<400> SEQUENCE: 41

Glu Gly Gln Val Thr Trp Leu
1               5

<210> SEQ ID NO 42
```

```
<211> LENGTH: 7
<212> TYPE: PRT
<213> ORGANISM: Artificial Sequence
<220> FEATURE:
<223> OTHER INFORMATION: Peptide sequence ERGHGWG for AAV capsid protein
      mutant

<400> SEQUENCE: 42

Glu Arg Gly His Gly Trp Gly
1               5

<210> SEQ ID NO 43
<211> LENGTH: 7
<212> TYPE: PRT
<213> ORGANISM: Artificial Sequence
<220> FEATURE:
<223> OTHER INFORMATION: Peptide sequence ESGVGWK for AAV capsid protein
      mutant

<400> SEQUENCE: 43

Glu Ser Gly Val Gly Trp Lys
1               5

<210> SEQ ID NO 44
<211> LENGTH: 7
<212> TYPE: PRT
<213> ORGANISM: Artificial Sequence
<220> FEATURE:
<223> OTHER INFORMATION: Peptide sequence GDGFGGV for AAV capsid protein
      mutant

<400> SEQUENCE: 44

Gly Asp Gly Phe Gly Gly Val
1               5

<210> SEQ ID NO 45
<211> LENGTH: 7
<212> TYPE: PRT
<213> ORGANISM: Artificial Sequence
<220> FEATURE:
<223> OTHER INFORMATION: Peptide sequence GDGVTWA for AAV capsid protein
      mutant

<400> SEQUENCE: 45

Gly Asp Gly Val Thr Trp Ala
1               5

<210> SEQ ID NO 46
<211> LENGTH: 7
<212> TYPE: PRT
<213> ORGANISM: Artificial Sequence
<220> FEATURE:
<223> OTHER INFORMATION: Peptide sequence GEGRGWV for AAV capsid protein
      mutant

<400> SEQUENCE: 46

Gly Glu Gly Arg Gly Trp Val
1               5

<210> SEQ ID NO 47
<211> LENGTH: 7
<212> TYPE: PRT
<213> ORGANISM: Artificial Sequence
<220> FEATURE:
<223> OTHER INFORMATION: Peptide sequence GGGDGWI for AAV capsid protein
      mutant

<400> SEQUENCE: 47
```

```
Gly Gly Gly Asp Gly Trp Ile
1               5

<210> SEQ ID NO 48
<211> LENGTH: 7
<212> TYPE: PRT
<213> ORGANISM: Artificial Sequence
<220> FEATURE:
<223> OTHER INFORMATION: Peptide sequence GGGDSWV for AAV capsid protein
      mutant

<400> SEQUENCE: 48

Gly Gly Gly Asp Ser Trp Val
1               5

<210> SEQ ID NO 49
<211> LENGTH: 12
<212> TYPE: PRT
<213> ORGANISM: Artificial Sequence
<220> FEATURE:
<223> OTHER INFORMATION: Peptide sequence GGGIAWVAQAAL for AAV capsid
      protein mutant

<400> SEQUENCE: 49

Gly Gly Gly Ile Ala Trp Val Ala Gln Ala Ala Leu
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Peptide sequence GGGVGWA for AAV capsid protein
      mutant

<400> SEQUENCE: 50

Gly Gly Gly Val Gly Trp Ala
1               5

<210> SEQ ID NO 51
<211> LENGTH: 7
<212> TYPE: PRT
<213> ORGANISM: Artificial Sequence
<220> FEATURE:
<223> OTHER INFORMATION: Peptide sequence GKGQVME for AAV capsid protein
      mutant

<400> SEQUENCE: 51

Gly Lys Gly Gln Val Met Glu
1               5

<210> SEQ ID NO 52
<211> LENGTH: 7
<212> TYPE: PRT
<213> ORGANISM: Artificial Sequence
<220> FEATURE:
<223> OTHER INFORMATION: Peptide sequence GNGTGGG for AAV capsid protein
      mutant

<400> SEQUENCE: 52

Gly Asn Gly Thr Gly Gly Gly
1               5

<210> SEQ ID NO 53
<211> LENGTH: 7
<212> TYPE: PRT
<213> ORGANISM: Artificial Sequence
<220> FEATURE:
```

<223> OTHER INFORMATION: Peptide sequence GQGGHME for AAV capsid protein
      mutant

<400> SEQUENCE: 53

Gly Gln Gly Gly His Met Glu
1               5

<210> SEQ ID NO 54
<211> LENGTH: 7
<212> TYPE: PRT
<213> ORGANISM: Artificial Sequence
<220> FEATURE:
<223> OTHER INFORMATION: Peptide sequence GRGVTWV for AAV capsid protein
      mutant

<400> SEQUENCE: 54

Gly Arg Gly Val Thr Trp Val
1               5

<210> SEQ ID NO 55
<211> LENGTH: 7
<212> TYPE: PRT
<213> ORGANISM: Artificial Sequence
<220> FEATURE:
<223> OTHER INFORMATION: Peptide sequence GSGMGWV for AAV capsid protein
      mutant

<400> SEQUENCE: 55

Gly Ser Gly Met Gly Trp Val
1               5

<210> SEQ ID NO 56
<211> LENGTH: 7
<212> TYPE: PRT
<213> ORGANISM: Artificial Sequence
<220> FEATURE:
<223> OTHER INFORMATION: Peptide sequence GVGGGVV for AAV capsid protein
      mutant

<400> SEQUENCE: 56

Gly Val Gly Gly Gly Val Val
1               5

<210> SEQ ID NO 57
<211> LENGTH: 7
<212> TYPE: PRT
<213> ORGANISM: Artificial Sequence
<220> FEATURE:
<223> OTHER INFORMATION: Peptide sequence NDVRGRV for AAV capsid protein
      mutant

<400> SEQUENCE: 57

Asn Asp Val Arg Gly Arg Val
1               5

<210> SEQ ID NO 58
<211> LENGTH: 7
<212> TYPE: PRT
<213> ORGANISM: Artificial Sequence
<220> FEATURE:
<223> OTHER INFORMATION: Peptide sequence RDGLGFV for AAV capsid protein
      mutant

<400> SEQUENCE: 58

Arg Asp Gly Leu Gly Phe Val
1               5

```
<210> SEQ ID NO 59
<211> LENGTH: 7
<212> TYPE: PRT
<213> ORGANISM: Artificial Sequence
<220> FEATURE:
<223> OTHER INFORMATION: Peptide sequence TDGLGWV for AAV capsid protein
      mutant

<400> SEQUENCE: 59

Thr Asp Gly Leu Gly Trp Val
1               5

<210> SEQ ID NO 60
<211> LENGTH: 7
<212> TYPE: PRT
<213> ORGANISM: Artificial Sequence
<220> FEATURE:
<223> OTHER INFORMATION: Peptide sequence TEGHGWV for AAV capsid protein
      mutant

<400> SEQUENCE: 60

Thr Glu Gly His Gly Trp Val
1               5

<210> SEQ ID NO 61
<211> LENGTH: 7
<212> TYPE: PRT
<213> ORGANISM: Artificial Sequence
<220> FEATURE:
<223> OTHER INFORMATION: Peptide sequence VAERLYG for AAV capsid protein
      mutant

<400> SEQUENCE: 61

Val Ala Glu Arg Leu Tyr Gly
1               5

<210> SEQ ID NO 62
<211> LENGTH: 7
<212> TYPE: PRT
<213> ORGANISM: Artificial Sequence
<220> FEATURE:
<223> OTHER INFORMATION: Peptide sequence VARGAGE for AAV capsid protein
      mutant

<400> SEQUENCE: 62

Val Ala Arg Gly Ala Gly Glu
1               5

<210> SEQ ID NO 63
<211> LENGTH: 9
<212> TYPE: PRT
<213> ORGANISM: Artificial Sequence
<220> FEATURE:
<223> OTHER INFORMATION: Peptide sequence GGSGVTWVA for AAV capsid
      protein mutant

<400> SEQUENCE: 63

Gly Gly Ser Gly Val Thr Trp Val Ala
1               5

<210> SEQ ID NO 64
<211> LENGTH: 9
<212> TYPE: PRT
<213> ORGANISM: Artificial Sequence
<220> FEATURE:
<223> OTHER INFORMATION: Peptide sequence GAHGYREPA for AAV capsid
      protein mutant

<400> SEQUENCE: 64
```

```
Gly Ala His Gly Tyr Arg Glu Pro Ala
1               5

<210> SEQ ID NO 65
<211> LENGTH: 9
<212> TYPE: PRT
<213> ORGANISM: Artificial Sequence
<220> FEATURE:
<223> OTHER INFORMATION: Peptide sequence GEYGFREGA for AAV capsid
      protein mutant

<400> SEQUENCE: 65

Gly Glu Tyr Gly Phe Arg Glu Gly Ala
1               5

<210> SEQ ID NO 66
<211> LENGTH: 9
<212> TYPE: PRT
<213> ORGANISM: Artificial Sequence
<220> FEATURE:
<223> OTHER INFORMATION: Peptide sequence GETGHGWVA for AAV capsid
      protein mutant

<400> SEQUENCE: 66

Gly Glu Thr Gly His Gly Trp Val Ala
1               5

<210> SEQ ID NO 67
<211> LENGTH: 9
<212> TYPE: PRT
<213> ORGANISM: Artificial Sequence
<220> FEATURE:
<223> OTHER INFORMATION: Peptide sequence GGGGIGYVA for AAV capsid
      protein mutant

<400> SEQUENCE: 67

Gly Gly Gly Gly Ile Gly Tyr Val Ala
1               5

<210> SEQ ID NO 68
<211> LENGTH: 9
<212> TYPE: PRT
<213> ORGANISM: Artificial Sequence
<220> FEATURE:
<223> OTHER INFORMATION: Peptide sequence GERGVGWVA for AAV capsid
      protein mutant

<400> SEQUENCE: 68

Gly Glu Arg Gly Val Gly Trp Val Ala
1               5

<210> SEQ ID NO 69
<211> LENGTH: 9
<212> TYPE: PRT
<213> ORGANISM: Artificial Sequence
<220> FEATURE:
<223> OTHER INFORMATION: Peptide sequence GENGVGWVA for AAV capsid
      protein mutant

<400> SEQUENCE: 69

Gly Glu Asn Gly Val Gly Trp Val Ala
1               5

<210> SEQ ID NO 70
<211> LENGTH: 9
<212> TYPE: PRT
<213> ORGANISM: Artificial Sequence
```

```
<220> FEATURE:
<223> OTHER INFORMATION: Peptide sequence GGSGVGWVA for AAV capsid
      protein mutant

<400> SEQUENCE: 70

Gly Gly Ser Gly Val Gly Trp Val Ala
1               5

<210> SEQ ID NO 71
<211> LENGTH: 9
<212> TYPE: PRT
<213> ORGANISM: Artificial Sequence
<220> FEATURE:
<223> OTHER INFORMATION: Peptide sequence GADGITWGA for AAV capsid
      protein mutant

<400> SEQUENCE: 71

Gly Ala Asp Gly Ile Thr Trp Gly Ala
1               5

<210> SEQ ID NO 72
<211> LENGTH: 9
<212> TYPE: PRT
<213> ORGANISM: Artificial Sequence
<220> FEATURE:
<223> OTHER INFORMATION: Peptide sequence GADGTRWVA for AAV capsid
      protein mutant

<400> SEQUENCE: 72

Gly Ala Asp Gly Thr Arg Trp Val Ala
1               5

<210> SEQ ID NO 73
<211> LENGTH: 9
<212> TYPE: PRT
<213> ORGANISM: Artificial Sequence
<220> FEATURE:
<223> OTHER INFORMATION: Peptide sequence GADKVGWVA for AAV capsid
      protein mutant

<400> SEQUENCE: 73

Gly Ala Asp Lys Val Gly Trp Val Ala
1               5

<210> SEQ ID NO 74
<211> LENGTH: 9
<212> TYPE: PRT
<213> ORGANISM: Artificial Sequence
<220> FEATURE:
<223> OTHER INFORMATION: Peptide sequence GAGGVGWTA for AAV capsid
      protein mutant

<400> SEQUENCE: 74

Gly Ala Gly Gly Val Gly Trp Thr Ala
1               5

<210> SEQ ID NO 75
<211> LENGTH: 9
<212> TYPE: PRT
<213> ORGANISM: Artificial Sequence
<220> FEATURE:
<223> OTHER INFORMATION: Peptide sequence GAGGVTGVA for AAV capsid
      protein mutant

<400> SEQUENCE: 75

Gly Ala Gly Gly Val Thr Gly Val Ala
1               5
```

```
<210> SEQ ID NO 76
<211> LENGTH: 9
<212> TYPE: PRT
<213> ORGANISM: Artificial Sequence
<220> FEATURE:
<223> OTHER INFORMATION: Peptide sequence GAGNAGGMA for AAV capsid
      protein mutant

<400> SEQUENCE: 76

Gly Ala Gly Asn Ala Gly Gly Met Ala
1               5

<210> SEQ ID NO 77
<211> LENGTH: 9
<212> TYPE: PRT
<213> ORGANISM: Artificial Sequence
<220> FEATURE:
<223> OTHER INFORMATION: Peptide sequence GAGQLGWVA for AAV capsid
      protein mutant

<400> SEQUENCE: 77

Gly Ala Gly Gln Leu Gly Trp Val Ala
1               5

<210> SEQ ID NO 78
<211> LENGTH: 9
<212> TYPE: PRT
<213> ORGANISM: Artificial Sequence
<220> FEATURE:
<223> OTHER INFORMATION: Peptide sequence GARGTEWEA for AAV capsid
      protein mutant

<400> SEQUENCE: 78

Gly Ala Arg Gly Thr Glu Trp Glu Ala
1               5

<210> SEQ ID NO 79
<211> LENGTH: 9
<212> TYPE: PRT
<213> ORGANISM: Artificial Sequence
<220> FEATURE:
<223> OTHER INFORMATION: Peptide sequence GDAGHGFVA for AAV capsid
      protein mutant

<400> SEQUENCE: 79

Gly Asp Ala Gly His Gly Phe Val Ala
1               5

<210> SEQ ID NO 80
<211> LENGTH: 9
<212> TYPE: PRT
<213> ORGANISM: Artificial Sequence
<220> FEATURE:
<223> OTHER INFORMATION: Peptide sequence GEANVGWVA for AAV capsid
      protein mutant

<400> SEQUENCE: 80

Gly Glu Ala Asn Val Gly Trp Val Ala
1               5

<210> SEQ ID NO 81
<211> LENGTH: 9
<212> TYPE: PRT
<213> ORGANISM: Artificial Sequence
<220> FEATURE:
<223> OTHER INFORMATION: Peptide sequence GECGLGEGA for AAV capsid
      protein mutant
```

```
<400> SEQUENCE: 81

Gly Glu Cys Gly Leu Gly Glu Gly Ala
1               5

<210> SEQ ID NO 82
<211> LENGTH: 9
<212> TYPE: PRT
<213> ORGANISM: Artificial Sequence
<220> FEATURE:
<223> OTHER INFORMATION: Peptide sequence GEGEVTWLA for AAV capsid
      protein mutant

<400> SEQUENCE: 82

Gly Glu Gly Glu Val Thr Trp Leu Ala
1               5

<210> SEQ ID NO 83
<211> LENGTH: 9
<212> TYPE: PRT
<213> ORGANISM: Artificial Sequence
<220> FEATURE:
<223> OTHER INFORMATION: Peptide sequence GEGGDGRVA for AAV capsid
      protein mutant

<400> SEQUENCE: 83

Gly Glu Gly Gly Asp Gly Arg Val Ala
1               5

<210> SEQ ID NO 84
<211> LENGTH: 9
<212> TYPE: PRT
<213> ORGANISM: Artificial Sequence
<220> FEATURE:
<223> OTHER INFORMATION: Peptide sequence GEGGFGEAA for AAV capsid
      protein mutant

<400> SEQUENCE: 84

Gly Glu Gly Gly Phe Gly Glu Ala Ala
1               5

<210> SEQ ID NO 85
<211> LENGTH: 6
<212> TYPE: PRT
<213> ORGANISM: Artificial Sequence
<220> FEATURE:
<223> OTHER INFORMATION: Peptide sequence GEGGGA for AAV capsid protein
      mutant

<400> SEQUENCE: 85

Gly Glu Gly Gly Gly Ala
1               5

<210> SEQ ID NO 86
<211> LENGTH: 9
<212> TYPE: PRT
<213> ORGANISM: Artificial Sequence
<220> FEATURE:
<223> OTHER INFORMATION: Peptide sequence GEGGMVWVA for AAV capsid
      protein mutant

<400> SEQUENCE: 86

Gly Glu Gly Gly Met Val Trp Val Ala
1               5

<210> SEQ ID NO 87
<211> LENGTH: 9
<212> TYPE: PRT
```

```
<213> ORGANISM: Artificial Sequence
<220> FEATURE:
<223> OTHER INFORMATION: Peptide sequence GEGGVGWTA for AAV capsid
      protein mutant

<400> SEQUENCE: 87

Gly Glu Gly Gly Val Gly Trp Thr Ala
1               5

<210> SEQ ID NO 88
<211> LENGTH: 9
<212> TYPE: PRT
<213> ORGANISM: Artificial Sequence
<220> FEATURE:
<223> OTHER INFORMATION: Peptide sequence GEGGVMWLA for AAV capsid
      protein mutant

<400> SEQUENCE: 88

Gly Glu Gly Gly Val Met Trp Leu Ala
1               5

<210> SEQ ID NO 89
<211> LENGTH: 9
<212> TYPE: PRT
<213> ORGANISM: Artificial Sequence
<220> FEATURE:
<223> OTHER INFORMATION: Peptide sequence GEGQVTWLA for AAV capsid
      protein mutant

<400> SEQUENCE: 89

Gly Glu Gly Gln Val Thr Trp Leu Ala
1               5

<210> SEQ ID NO 90
<211> LENGTH: 9
<212> TYPE: PRT
<213> ORGANISM: Artificial Sequence
<220> FEATURE:
<223> OTHER INFORMATION: Peptide sequence GERGHGWGA for AAV capsid
      protein mutant

<400> SEQUENCE: 90

Gly Glu Arg Gly His Gly Trp Gly Ala
1               5

<210> SEQ ID NO 91
<211> LENGTH: 9
<212> TYPE: PRT
<213> ORGANISM: Artificial Sequence
<220> FEATURE:
<223> OTHER INFORMATION: Peptide sequence GESGVGWKA for AAV capsid
      protein mutant

<400> SEQUENCE: 91

Gly Glu Ser Gly Val Gly Trp Lys Ala
1               5

<210> SEQ ID NO 92
<211> LENGTH: 9
<212> TYPE: PRT
<213> ORGANISM: Artificial Sequence
<220> FEATURE:
<223> OTHER INFORMATION: Peptide sequence GGDGFGGVA for AAV capsid
      protein mutant

<400> SEQUENCE: 92

Gly Gly Asp Gly Phe Gly Gly Val Ala
1               5
```

<210> SEQ ID NO 93
<211> LENGTH: 9
<212> TYPE: PRT
<213> ORGANISM: Artificial Sequence
<220> FEATURE:
<223> OTHER INFORMATION: Peptide sequence GGDGVTWAA for AAV capsid
      protein mutant

<400> SEQUENCE: 93

Gly Gly Asp Gly Val Thr Trp Ala Ala
1               5

<210> SEQ ID NO 94
<211> LENGTH: 9
<212> TYPE: PRT
<213> ORGANISM: Artificial Sequence
<220> FEATURE:
<223> OTHER INFORMATION: Peptide sequence GGEGRGWVA for AAV capsid
      protein mutant

<400> SEQUENCE: 94

Gly Gly Glu Gly Arg Gly Trp Val Ala
1               5

<210> SEQ ID NO 95
<211> LENGTH: 9
<212> TYPE: PRT
<213> ORGANISM: Artificial Sequence
<220> FEATURE:
<223> OTHER INFORMATION: Peptide sequence GGGGDGWIA for AAV capsid
      protein mutant

<400> SEQUENCE: 95

Gly Gly Gly Gly Asp Gly Trp Ile Ala
1               5

<210> SEQ ID NO 96
<211> LENGTH: 9
<212> TYPE: PRT
<213> ORGANISM: Artificial Sequence
<220> FEATURE:
<223> OTHER INFORMATION: Peptide sequence GGGGDSWVA for AAV capsid
      protein mutant

<400> SEQUENCE: 96

Gly Gly Gly Gly Asp Ser Trp Val Ala
1               5

<210> SEQ ID NO 97
<211> LENGTH: 14
<212> TYPE: PRT
<213> ORGANISM: Artificial Sequence
<220> FEATURE:
<223> OTHER INFORMATION: Peptide sequence GGGGIAWVAQAALA for AAV capsid
      protein mutant

<400> SEQUENCE: 97

Gly Gly Gly Gly Ile Ala Trp Val Ala Gln Ala Ala Leu Ala
1               5                   10

<210> SEQ ID NO 98
<211> LENGTH: 9
<212> TYPE: PRT
<213> ORGANISM: Artificial Sequence
<220> FEATURE:
<223> OTHER INFORMATION: Peptide sequence GGGGVGWAA for AAV capsid
      protein mutant

```
<400> SEQUENCE: 98

Gly Gly Gly Gly Val Gly Trp Ala Ala
1               5

<210> SEQ ID NO 99
<211> LENGTH: 9
<212> TYPE: PRT
<213> ORGANISM: Artificial Sequence
<220> FEATURE:
<223> OTHER INFORMATION: Peptide sequence GGKGQVMEA for AAV capsid
      protein mutant

<400> SEQUENCE: 99

Gly Gly Lys Gly Gln Val Met Glu Ala
1               5

<210> SEQ ID NO 100
<211> LENGTH: 9
<212> TYPE: PRT
<213> ORGANISM: Artificial Sequence
<220> FEATURE:
<223> OTHER INFORMATION: Peptide sequence GGNGTGGGA for AAV capsid
      protein mutant

<400> SEQUENCE: 100

Gly Gly Asn Gly Thr Gly Gly Gly Ala
1               5

<210> SEQ ID NO 101
<211> LENGTH: 9
<212> TYPE: PRT
<213> ORGANISM: Artificial Sequence
<220> FEATURE:
<223> OTHER INFORMATION: Peptide sequence GGQGGHMEA for AAV capsid
      protein mutant

<400> SEQUENCE: 101

Gly Gly Gln Gly Gly His Met Glu Ala
1               5

<210> SEQ ID NO 102
<211> LENGTH: 9
<212> TYPE: PRT
<213> ORGANISM: Artificial Sequence
<220> FEATURE:
<223> OTHER INFORMATION: Peptide sequence GGRGVTWVA for AAV capsid
      protein mutant

<400> SEQUENCE: 102

Gly Gly Arg Gly Val Thr Trp Val Ala
1               5

<210> SEQ ID NO 103
<211> LENGTH: 9
<212> TYPE: PRT
<213> ORGANISM: Artificial Sequence
<220> FEATURE:
<223> OTHER INFORMATION: Peptide sequence GGSGMGWVA for AAV capsid
      protein mutant

<400> SEQUENCE: 103

Gly Gly Ser Gly Met Gly Trp Val Ala
1               5

<210> SEQ ID NO 104
<211> LENGTH: 9
```

-continued

```
<212> TYPE: PRT
<213> ORGANISM: Artificial Sequence
<220> FEATURE:
<223> OTHER INFORMATION: Peptide sequence GGVGGGVVA for AAV capsid
      protein mutant

<400> SEQUENCE: 104

Gly Gly Val Gly Gly Gly Val Val Ala
1               5

<210> SEQ ID NO 105
<211> LENGTH: 9
<212> TYPE: PRT
<213> ORGANISM: Artificial Sequence
<220> FEATURE:
<223> OTHER INFORMATION: Peptide sequence GNDVRGRVA for AAV capsid
      protein mutant

<400> SEQUENCE: 105

Gly Asn Asp Val Arg Gly Arg Val Ala
1               5

<210> SEQ ID NO 106
<211> LENGTH: 9
<212> TYPE: PRT
<213> ORGANISM: Artificial Sequence
<220> FEATURE:
<223> OTHER INFORMATION: Peptide sequence GRDGLGFVA for AAV capsid
      protein mutant

<400> SEQUENCE: 106

Gly Arg Asp Gly Leu Gly Phe Val Ala
1               5

<210> SEQ ID NO 107
<211> LENGTH: 9
<212> TYPE: PRT
<213> ORGANISM: Artificial Sequence
<220> FEATURE:
<223> OTHER INFORMATION: Peptide sequence GTDGLGWVA for AAV capsid
      protein mutant

<400> SEQUENCE: 107

Gly Thr Asp Gly Leu Gly Trp Val Ala
1               5

<210> SEQ ID NO 108
<211> LENGTH: 9
<212> TYPE: PRT
<213> ORGANISM: Artificial Sequence
<220> FEATURE:
<223> OTHER INFORMATION: Peptide sequence GTEGHGWVA for AAV capsid
      protein mutant

<400> SEQUENCE: 108

Gly Thr Glu Gly His Gly Trp Val Ala
1               5

<210> SEQ ID NO 109
<211> LENGTH: 9
<212> TYPE: PRT
<213> ORGANISM: Artificial Sequence
<220> FEATURE:
<223> OTHER INFORMATION: Peptide sequence GVAERLYGA for AAV capsid
      protein mutant

<400> SEQUENCE: 109

Gly Val Ala Glu Arg Leu Tyr Gly Ala
```

```
1               5

<210> SEQ ID NO 110
<211> LENGTH: 9
<212> TYPE: PRT
<213> ORGANISM: Artificial Sequence
<220> FEATURE:
<223> OTHER INFORMATION: Peptide sequence GVARGAGEA for AAV capsid
      protein mutant

<400> SEQUENCE: 110

Gly Val Ala Arg Gly Ala Gly Glu Ala
1               5

<210> SEQ ID NO 111
<211> LENGTH: 7
<212> TYPE: PRT
<213> ORGANISM: Artificial Sequence
<220> FEATURE:
<223> OTHER INFORMATION: Peptide sequence represented by Formula I
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 111

Xaa Xaa Gly Xaa Gly Trp Val
1               5

<210> SEQ ID NO 112
<211> LENGTH: 7
<212> TYPE: PRT
<213> ORGANISM: Artificial Sequence
<220> FEATURE:
<223> OTHER INFORMATION: Peptide sequence represented by Formula II
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 112

Xaa Xaa Xaa Xaa Gly Trp Val
1               5

<210> SEQ ID NO 113
<211> LENGTH: 7
<212> TYPE: PRT
<213> ORGANISM: Artificial Sequence
<220> FEATURE:
<223> OTHER INFORMATION: Peptide sequence represented by Formula III
<220> FEATURE:
<221> NAME/KEY: MOD_RES
```

```
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (5)..(5)
<223> OTHER INFORMATION: Any amino acid

<400> SEQUENCE: 113

Xaa Xaa Gly Xaa Xaa Trp Val
1               5

<210> SEQ ID NO 114
<211> LENGTH: 7
<212> TYPE: PRT
<213> ORGANISM: Artificial Sequence
<220> FEATURE:
<223> OTHER INFORMATION: Peptide sequence represented by Formula IV
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 114

Xaa Xaa Gly Xaa Gly Xaa Val
1               5

<210> SEQ ID NO 115
<211> LENGTH: 7
<212> TYPE: PRT
<213> ORGANISM: Artificial Sequence
<220> FEATURE:
<223> OTHER INFORMATION: Peptide sequence represented by Formula V
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 115

Xaa Xaa Gly Xaa Gly Trp Xaa
1               5
```

-continued

```
<210> SEQ ID NO 116
<211> LENGTH: 7
<212> TYPE: PRT
<213> ORGANISM: Artificial Sequence
<220> FEATURE:
<223> OTHER INFORMATION: Peptide sequence represented by Formula VI
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 116

Xaa Xaa Gly Xaa Arg Glu Xaa
1               5
```